(12) United States Patent
Kehler et al.

(10) Patent No.: US 8,138,220 B2
(45) Date of Patent: Mar. 20, 2012

(54) [2-(6-FLUORO-1H-INDOL-3-YLSULFANYL)-BENZYL]METHYL AMINE FOR THE TREATMENT OF AFFECTIVE DISORDERS

(75) Inventors: Jan Kehler, Lyngby (DK); Karsten Juhl, Greve (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 12/438,734

(22) PCT Filed: Sep. 27, 2007

(86) PCT No.: PCT/DK2007/000419
§ 371 (c)(1),
(2), (4) Date: May 14, 2009

(87) PCT Pub. No.: WO2008/037258
PCT Pub. Date: Apr. 3, 2008

(65) Prior Publication Data
US 2009/0326036 A1    Dec. 31, 2009

Related U.S. Application Data

(60) Provisional application No. 60/827,292, filed on Sep. 28, 2006, provisional application No. 60/862,402, filed on Oct. 20, 2006.

(30) Foreign Application Priority Data

Sep. 28, 2006 (DK) .......................... PA 2006 01251
Mar. 20, 2007 (DK) .......................... PA 2007 00432

(51) Int. Cl.
*A61K 31/404* (2006.01)
*C07D 207/36* (2006.01)
(52) U.S. Cl. ...................... 514/418; 548/484
(58) Field of Classification Search .................... 548/484
See application file for complete search history.

(56) References Cited

U.S. PATENT DOCUMENTS

| 2008/0176922 A1 | 7/2008 | Kehler et al. |
| 2008/0214644 A1 | 9/2008 | Kehler et al. |
| 2008/0214645 A1 | 9/2008 | Kehler et al. |

FOREIGN PATENT DOCUMENTS

| WO | 2005/061455 A1 | 7/2005 |
| WO | WO 2005/061455 A1 * | 7/2005 |
| WO | 2007/107165 A1 | 9/2007 |

OTHER PUBLICATIONS

Obsessive Compulsive Disorder [online] retrieved on Jan. 18, 2011 from the internet. URL; http://www.webmd.com/anxiety-panic/guide/obsessive-compulsive-disorder?page=3.*
Morissette, et al. Advanced Drug Delivery Reviews 56 (2004) 275-300.*
Fibromyalgia [online] retrieved from internet on Jul. 31, 2011. URL; http://www.mayoclinic.com/health/fibromyalgia/DS00079.*
Nelson et al., "Nonhormonal Therapies for Menopausal Hot Flashes," JAMA, (May 3, 2006), vol. 295, No. 17, pp. 2057-2071.
Thase, "Effects of Venlafaxine on Blood Pressure: A Meta-Analysis of Original Data from 3744 Depressed Patients," J Clin Psychiatry 59:10, Oct. 1998, pp. 502-508.
Ostacher, "The Evidence for Antidepressant Use in Bipolar Depression," J Clin Psychiatry (2006); 67, pp. 18-21.
Keinke et al., "Efficacy of Venlafaxine in the Treatment of Severe Depression," Depression and Anxiety, vol. 12, supplement 1:50-54 (2000).
Raskind et al., "A Parallel Group Placebo Controlled Study of Prazosin for Trauma Nightmares and Sleep Disturbance in Combat Veterans with Post-Traumatic Stress Disorder", Biol Psychiatry (2007); 61:928-934.
Lowe, Rose of the Newer Alpha,-Adrenergic-Receptor Antagonists in the Treatment of Benign Prostatic Hyperplasia-Related Lower Urinary Tract Symptoms, Clinical Therapeutics, vol. 26, No. 11 (2004), pp. 1701-1713.
Dunner et al., "Clinical Consequences of Initial Duloxetine Dosing Strategies: Comparison of 30 and 60 mg QD Starting Doses", Current Therapeutic Research, vol. 66, No. 6, (Nov./Dec. 2005), pp. 522-540.
Mashiko et al., "Effect of trazodone in a single dose before bedtime for sleep disorders accompanied by a depressive state: Dose-finding study with no concomitant use of hypnotic agent", Psychiatry and Clinical Neurosciences (1999), 53, pp. 193-194.
Rush et al., "Comparative Effects of nefazodone and Fluoxetine on Sleep in Outpatients with Major Depressive Disorder," Society of Biological Psychiatry (1998), pp. 3-14.
Viola et al., "Ritanserin, a serotonini-2 receptor antagonist, improves ultradian sleep rhythmicity in young poor sleepers", Clinical Neurophysiology 113 (2002) 429-434.
Fish et al., "4-Fluorosulfonylpiperidines: Selective $5-HT_{2A}$ ligands for the treatment of insomnia", Bioorganic & Medicinal Chemistry Letters 15 (2005) 3665-3669.
Mayers et al., "Antidepressants and their effect on sleep", Human Psychopharmacology Clin Exp (2005) 20, 533-559.
Lam "Sleep distrubances and depression: a challenge for antidepressants" International Clinical Psychopharmacology (2006), 21 (suppl 1):S25-S29.
Label for Cymbalta (duloxetine hydrochloride) delayed release capsules, Eli Lilly and Company, Indianapolis, IN, 2004, 2011, Literature revised May 6, 2011, 25 pages.
Label for Effexor (venlafaxine hydrochloride) tablets, Wyeth Pharmaceuticals Inc., Philadelphia, PA, Revised Jun. 2006, 34 pages.
Label for Effexor XR (venlafaxine hydrochloride) extended release tablets, Wyeth Pharmaceuticals Inc., Philadelphia, PA, Revised Jun. 2006, 47 pages.

* cited by examiner

*Primary Examiner* — Shawquia Young
(74) *Attorney, Agent, or Firm* — Fish & Richardson P.C.

(57) ABSTRACT

[2-(6-fluoro-1H-indol-3-ylsulfanyl)benzyl]methyl amine and pharmaceutically acceptable salts thereof, provided it is not the free base in a non-crystalline form are provided for the treatment of affective disorders.

6 Claims, 44 Drawing Sheets

Acetic acid 1:1 α-form

Acetic acid 1:1 β-form

Propionic acid 1:1

2-hydroxy isobutyric acid 1:1

Adipic acid 2:1 α+β

Adipic acid 2:1 β-form

Adipic acid 2:1 γ-form

Fumaric acid 2:1 α+β

Fumaric acid 2:1 α-form

Fumaric acid 2:1 γ-form

Fumaric acid: mixture/solvate

Maleic acid 2:1 α-form

Maleic acid: mixture/solvate

Malonic acid 2:1

Malic acid 2:1 α-form

Malic acid 2:1 α and β

Malic acid 2:1 γ-form

Glutaric acid 2:1

Oxalic acid 2:1 α-form

Oxalic acid 2:1 β-form

Oxalic acid, mixture

Sebacic acid 2:1 β-form

Sebacic acid 2:1 γ-form

Sebacic acid, mixture/solvate

Succinic acid 2:1 β-form

Succinic acid 2:1 γ-form

Succinic acid, mixture/solvate

HBr 1:1

M-tartaric acid 2:1 α-form

M-tartaric acid, mixture/solvate 2-oxoglutaric acid 2:1

Phosphoric acid, mixture/solvate

Glutaminic acid, mixture/solvate

Figure 1:
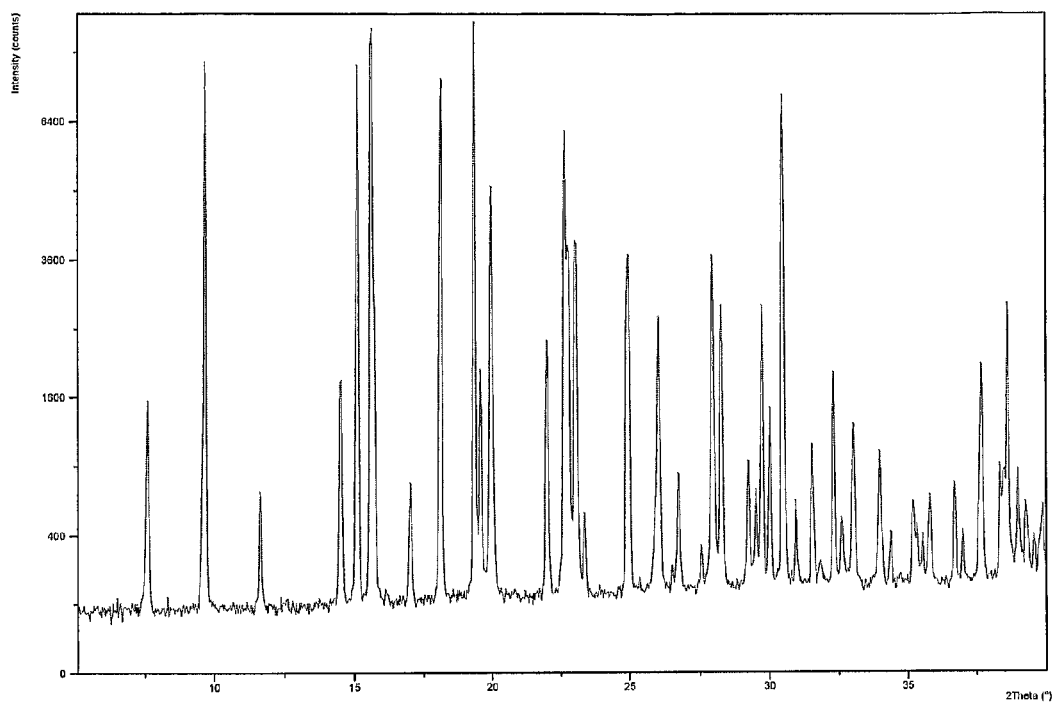

[2-(6-FLUORO-1H-INDOL-3-YLSULFANYL)-BENZYL]METHYL AMINE FOR THE TREATMENT OF AFFECTIVE DISORDERS

CROSS REFERENCE TO PRIOR APPLICATIONS

This is the U.S. National Phase application under 35 U.S.C. §371 of International Patent Application No. PCT/DK2007/000419, filed Sep. 27, 2007, and claims the benefit of Danish Application No. PA 200601251, filed Sep. 28, 2006, U.S. Provisional Application No. 60/872,292, filed Sep. 28, 2006, U.S. Provisional Application No. 60/862,407, filed Oct. 20, 2006, and Danish Application No. PA 200700432, filed Mar. 20, 2007, all of which are incorporated by reference herein. The International Application published in English on Apr. 3, 2008 as WO 2008/037258 under PCT Article 21(2).

FIELD OF THE INVENTION

The present invention provides compounds useful for therapeutic treatment

BACKGROUND OF THE INVENTION

Sleep is a vital factor in many affective disorders, such as e.g. depression and the treatment of depression. In fact, sleep disruption is a major symptom of depression, and often it is the sleep disruption that causes a patient suffering from depression to seek help. In light of this, it is important that any medical intervention offered to the depressed patient ameliorates the sleep disturbances and, certainly, that it does not itself add to the sleep problems. The same, of course holds true for the treatment of other affective disorders.

Standard medical treatment of affective disorders includes compounds having the effect of increasing the level of the monoamine neurotransmitters serotonin and/or noradrenaline in the brain. Despite the fact that these medicaments are used for the treatment of a wide variety of affective disorders, they are normally referred to as "antidepressants". The most wide spread treatment modalities include selective serotonin reuptake inhibitors (SSRI) which increase the level of serotonin, well-known and marketed examples of which include escitalopram, fluoxetine and setraline. Selective noradrenalin reuptake inhibitors (NRI) increase the level of noradrenalin, one example of which is reboxetine. Other compounds inhibit both the serotonin and the noradrenalin reuptake and are referred to as SNRI. Prominent examples of this group of medicaments include venlafaxine and duloxetine. Finally, the group of medicaments referred to as tri-cyclic amines (TCA) is widely used in the treatment of depression, and members of this group of compounds tend to have a broader pharmacological profile with an effect on other brain receptors, such as acetylcholine, adrenergic and histamine receptors, on top of an inhibiting effect on the serotonin and noradrenalin transporters.

Unfortunately, sleep disturbances seem to be a general adverse affect of most antidepressants. In particular, SSRI, NRI and SNRI are reported to give rise to problems with sleep initiation and maintenance and problems with insomnia are often reported, too [*Int. Clin. Psychpharm.*, 21 (suppl 1), S25-S29, 2006]. Others report that such compounds give rise to suppressed REM sleep, increased sleep latency, less efficient sleep, increase in nocturnal awakenings, and fragmentation of sleep [*Hum. Psychopharm. Clin. Exp.*, 20, 533-559, 2005].

It is generally speculated that the adverse sleep effects are caused by stimulation of the $5\text{-HT}_{2A}$ receptor. R. L. Fish reports in *Bioorg. Med. Chem. Lett.*, 15, 3665-3669, 2005 that certain 4-fluorosulfonylpiperidines, which are highly selective $5\text{-HT}_{2A}$ antagonists are effective in increasing the slow wave sleep duration and decreasing the number of awakenings in rats. These pre-clinical observations are confirmed by clinical findings. Ritanserin, a $5\text{-HT}_{2A}$ antagonist, has been shown to increase the total sleep time, the slow wave sleep duration, the REM sleep duration, and improve the subjective sleep quality in humans [*Clin. Neurophys.* 113, 429-434, 2002]. Nefazodone, a potent inhibitor of $5\text{-HT}_{2A}$ and a weak inhibitor of the serotonin and the noradrenalin reuptake, has in clinical trials been shown to increase sleep continuity and total REM sleep time, and to reduce the number of awakenings [*Biol. Psychiatry*, 44, 3-14, 1998]. Similarly, trazodone, which is a $5\text{-HT}_{2A}$ antagonist and a moderate inhibitor of the serotonin reuptake, has been shown to improve the clinical scores HAS (sleep disorders) and HRSD (premature morning awakening, lack of sound sleep and initiating sleep) [*Psychiatr. Clin. Neurosci.*, 53, 193-194, 1999].

The above findings and observations suggest that the identification of compounds having an inhibitory effect of the serotonin and/or noradrenalin reuptake in combination with a $5\text{-HT}_{2A}$ antagonistic activity would provide compounds suitable for the treatment of affective disorders, such as e.g. depression, without or with reduced adverse sleep effects, or wherein the sleep quality of the depressed patient is even improved.

The use of compounds having noradrenalin reuptake inhibitory effects brings about an increase in the level of noradrenalin, which is the cause of the therapeutic effect in the treatment of affective disorders. Noradrenalin, however, also has peripheral effects, e.g. increased heart rate, blood vessel constriction and a consequent increase in blood pressure. These peripheral effects transpire in the adverse effects reported for noradrenalin reuptake inhibitors. Venlafaxine and duloxetine, both of which are noradrenalin and serotonin reuptake inhibitors, are reported to give rise to an increase in blood pressure [*Curr. Ther. Res.*, 66, 522-540, 2005; *J. Clin. Psychiatry*, 59, 502-508, 1998]. An increase in blood pressure is problematic in general, and in patients already suffering from increased blood pressure (hypertensives), e.g. elderly people, in particular.

Antagonists of the $alpha_1$ adrenergic receptor ($\alpha_1$ receptor) are known to give rise to peripheral vasodilation and the consequent reduction in blood pressure due to reduced flow resistance [*Clin Ther.*, 26, 1701-1713, 2004].

The above findings and observations suggest that the identification of compounds having an inhibitory effect on the serotonin and/or noradrenalin reuptake in combination with a $\alpha_1$ receptor antagonistic activity would provide compounds suitable for the treatment of affective disorders, such as e.g. depression, without or with reduced adverse cardiovascular effects, such as e.g. increased blood pressure.

The international patent application published as WO 2005/061455 discloses that certain 2-(1H-indolylsulfanyl) benzyl amine derivatives, and in particular [2-(6-fluoro-1H-indol-3-ylsulfanyl)benzyl]methyl amine are serotonin reuptake inhibitors and probably also noradrenalin reuptake inhibitors. The compounds are said to be useful for the treatment of affective disorders, such as e.g. depression.

SUMMARY OF THE INVENTION

The present inventors have surprisingly found that [2-(6-fluoro-1H-indol-3-ylsulfanyl)benzyl]methyl amine is a potent serotonin reuptake inhibitor, a potent noradrenalin reuptake inhibitor, a potent $5\text{-HT}_{2A}$ antagonist and a potent α$_{1A}$ receptor antagonist, and as such useful in the treatment of affective disorders avoiding or reducing sleep related adverse effects, or even improving the sleep quality of the patient, and/or avoiding or reducing cardiovascular side effects. Accordingly, in one embodiment, the invention relates to compound I, which is [2-(6-fluoro-1H-indol-3-ylsulfanyl) benzyl]methyl amine

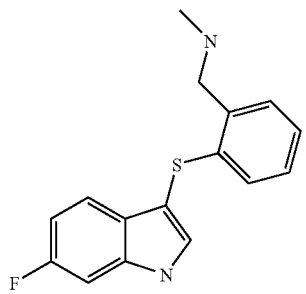

[I]

and pharmaceutically acceptable salts thereof, provided said compound is not the free base in a non-crystalline form.

In one embodiment, the invention relates to compound I for use in therapy.

In one embodiment, the invention relates to a pharmaceutical composition comprising a compound of the present invention in combination with a pharmaceutically acceptable carrier or excipient.

In one embodiment, the invention relates to methods of treatment, the method comprising the administration of a therapeutically effective amount of compound I to a patient in need thereof.

In one embodiment, the invention relates to the use of compound I in the manufacture of a medicament.

FIGURES

Figure 3:
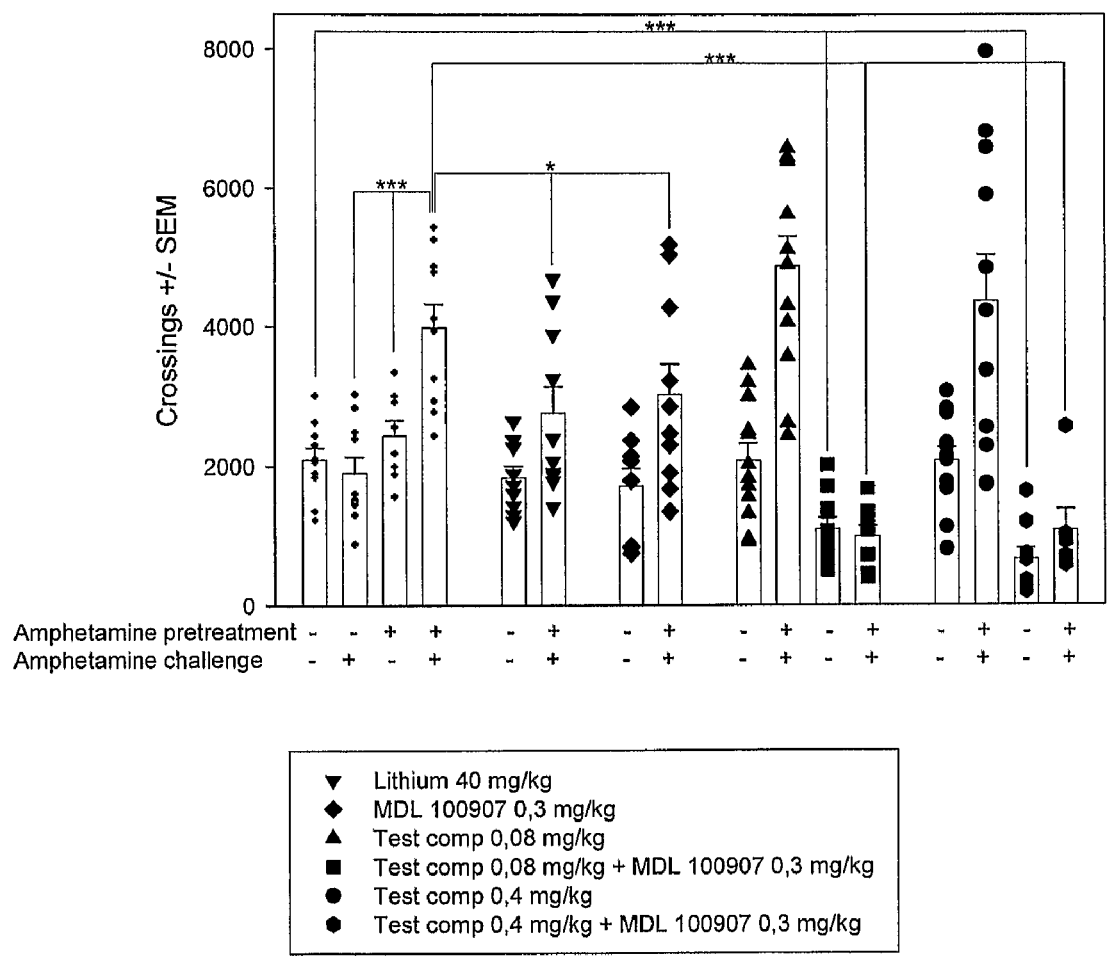
Figure 4:
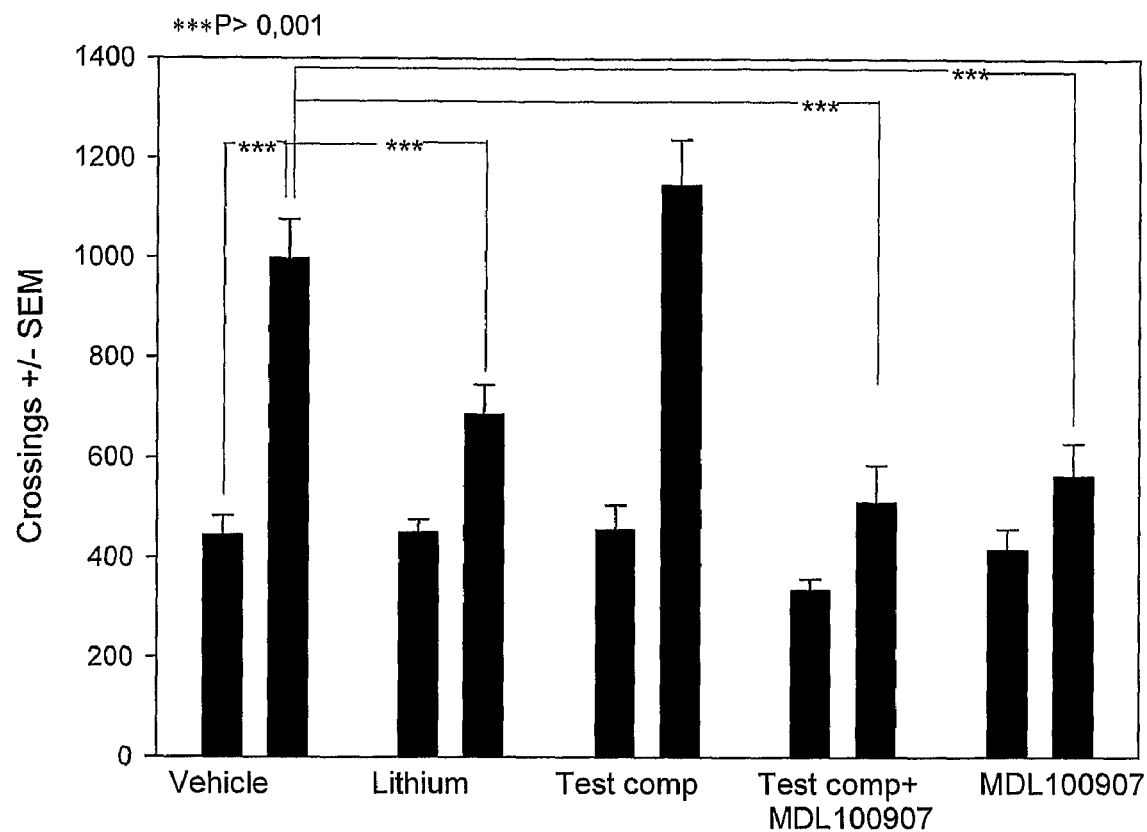
Figure 7:
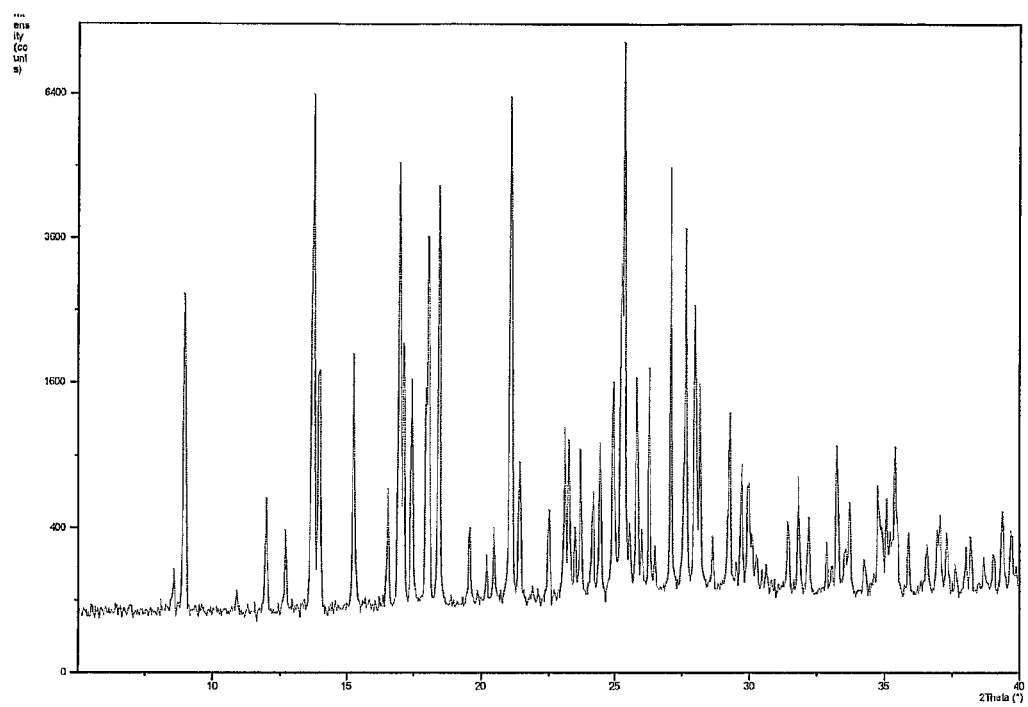
Figure 8:
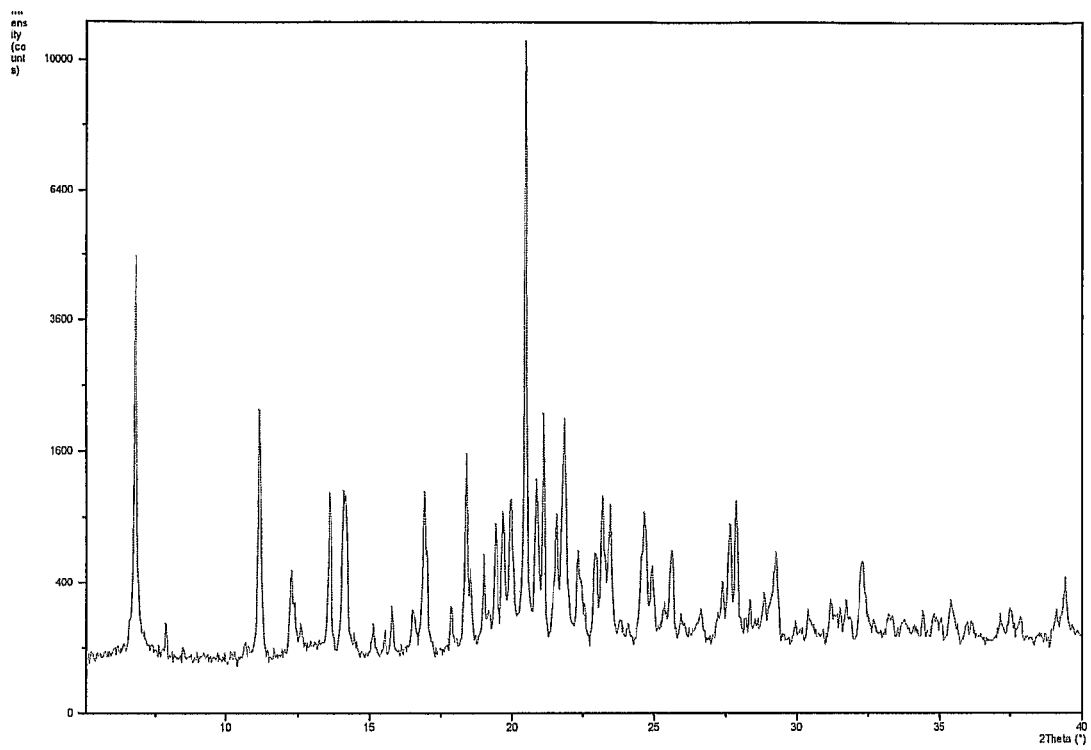
Figure 9:
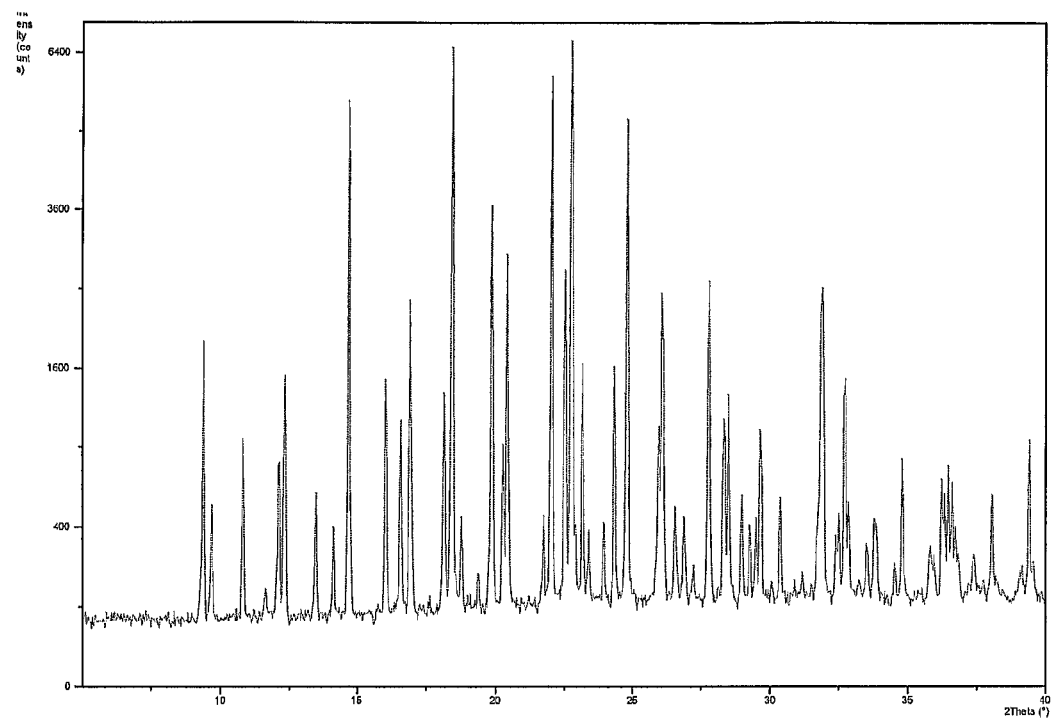
Figure 10:
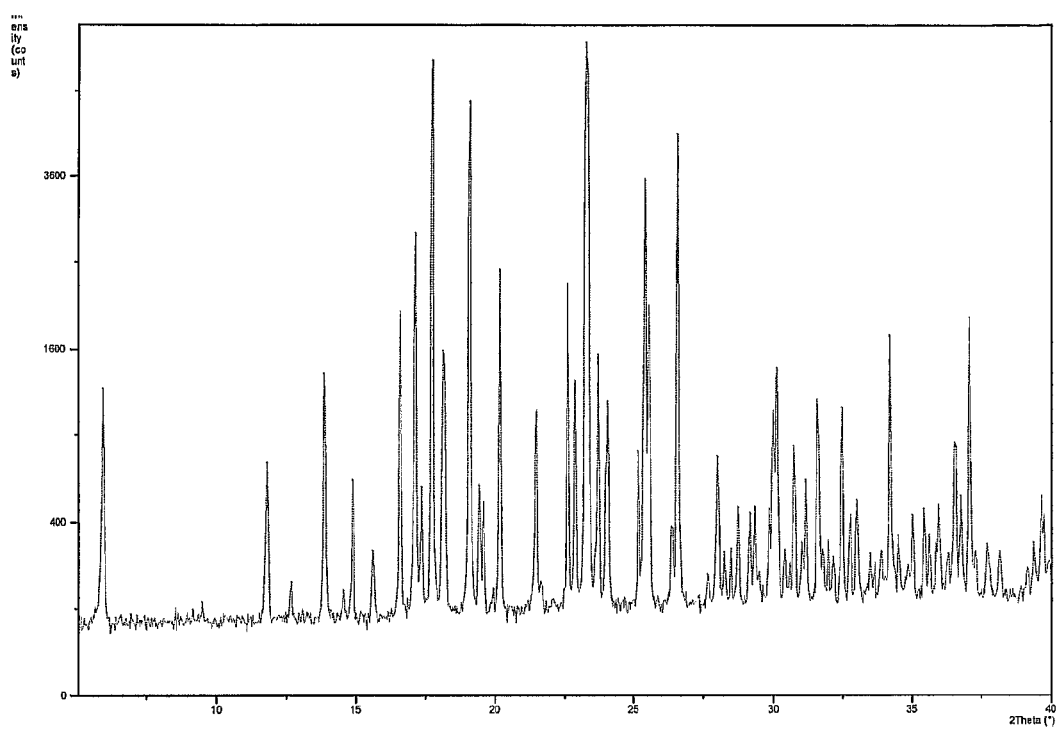
Figure 11:
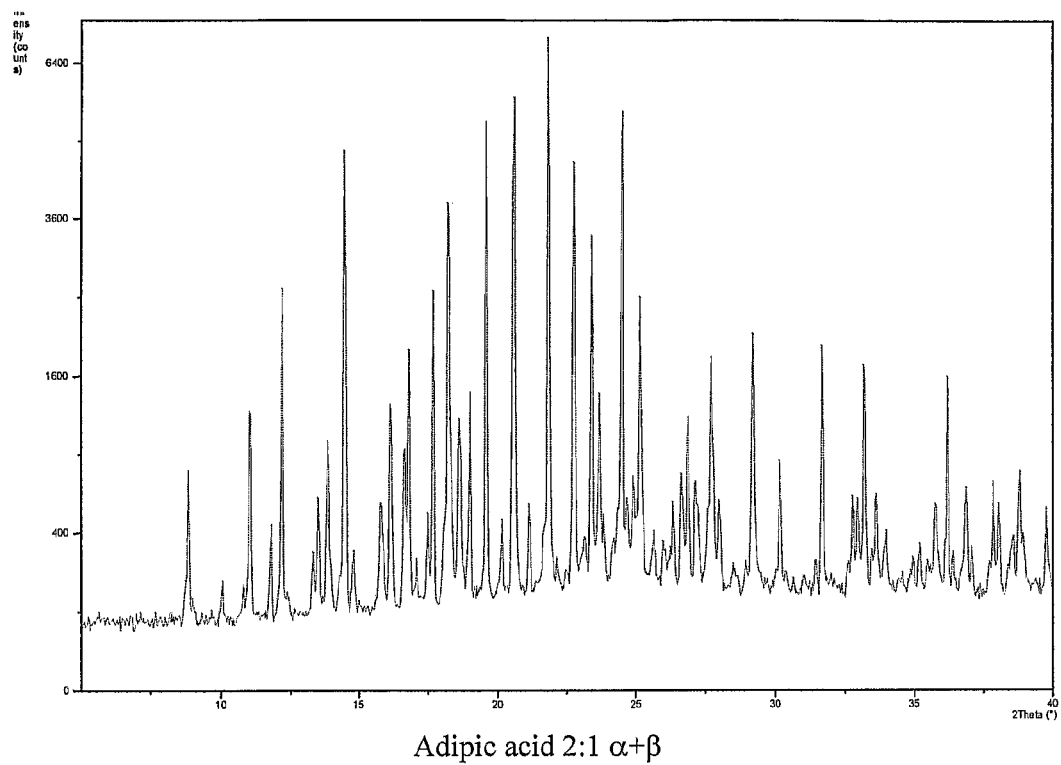
Figure 12:
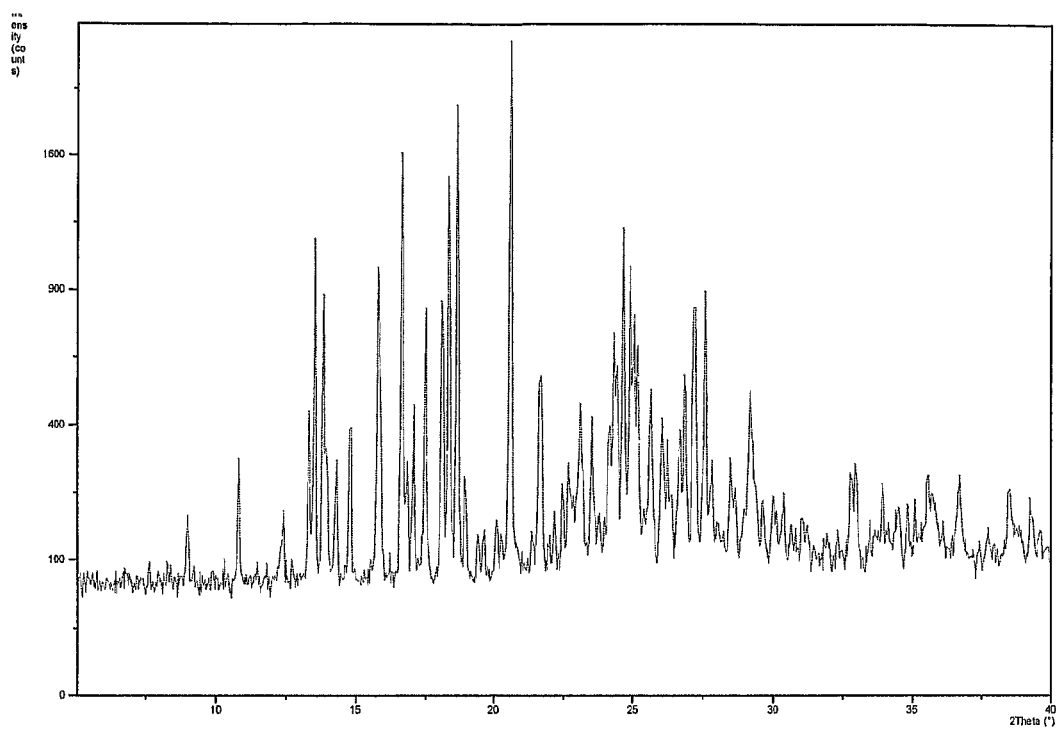
Figure 13:
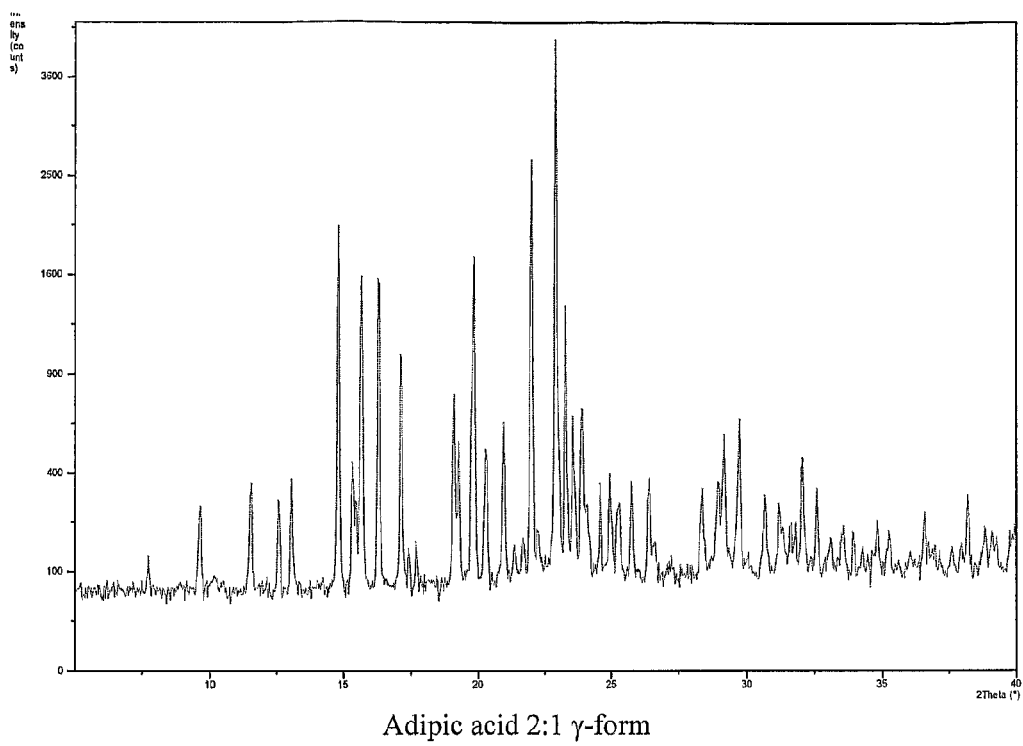
Figure 14:
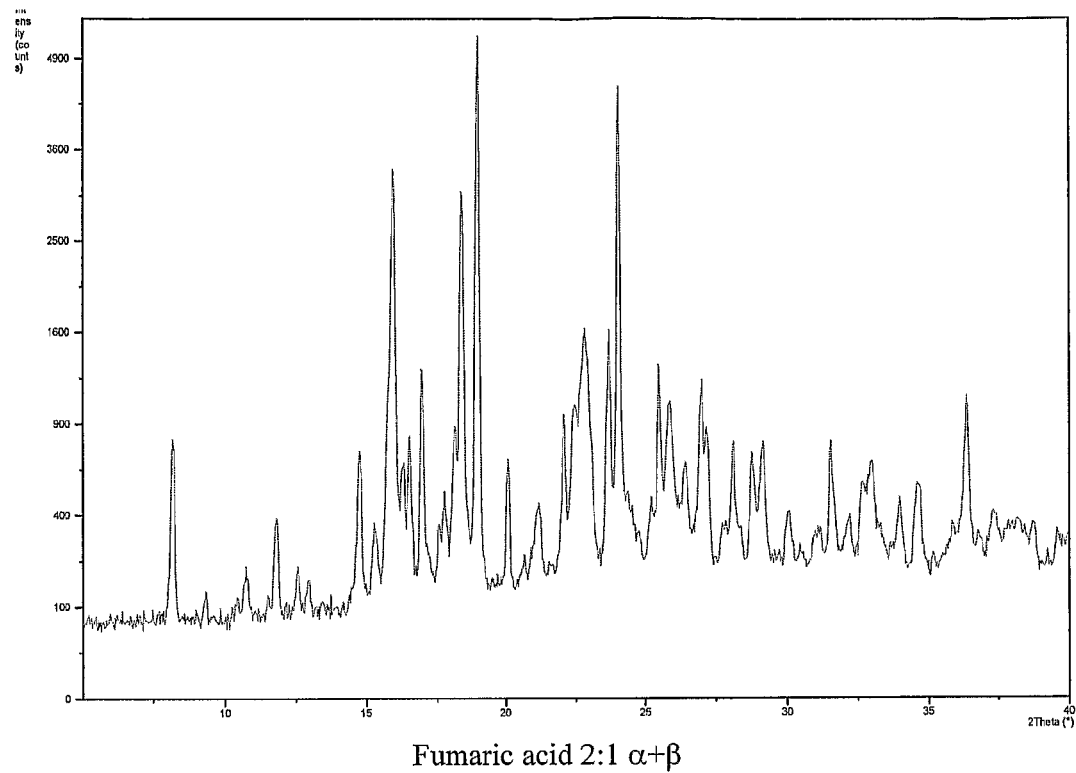
Figure 15:
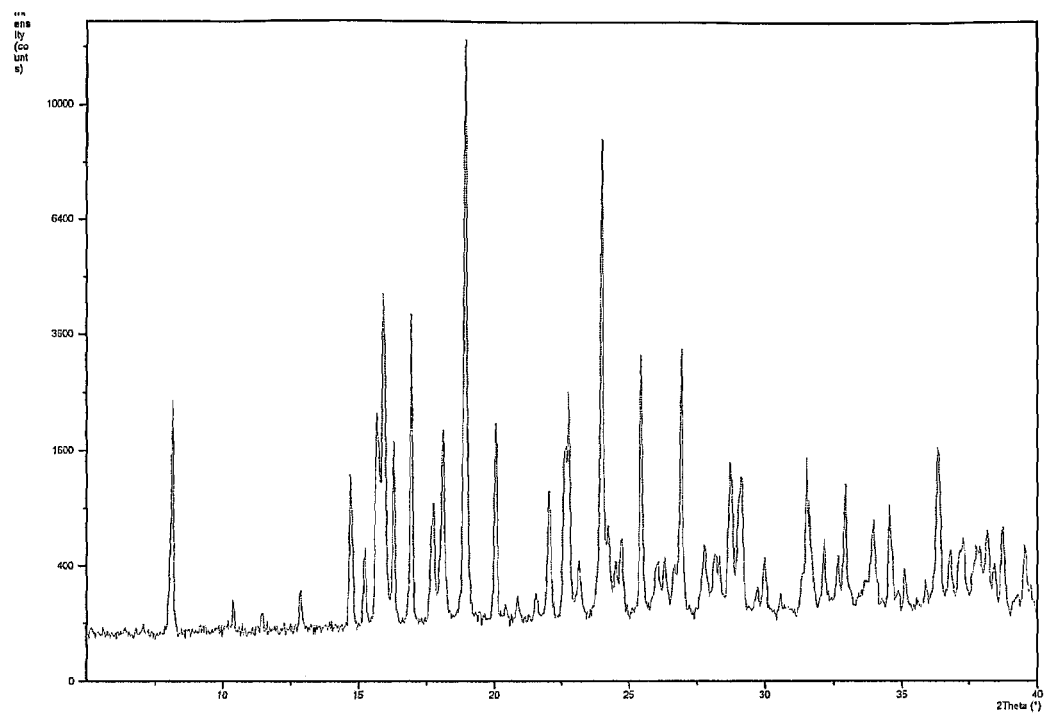
Figure 16:
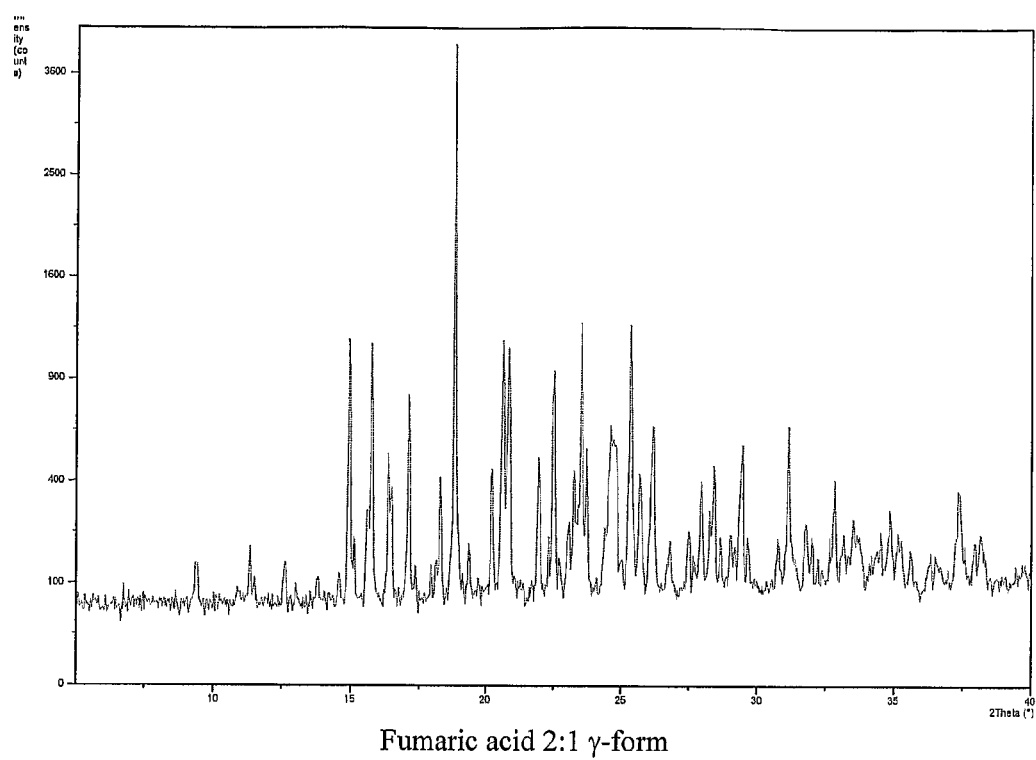
Figure 17:
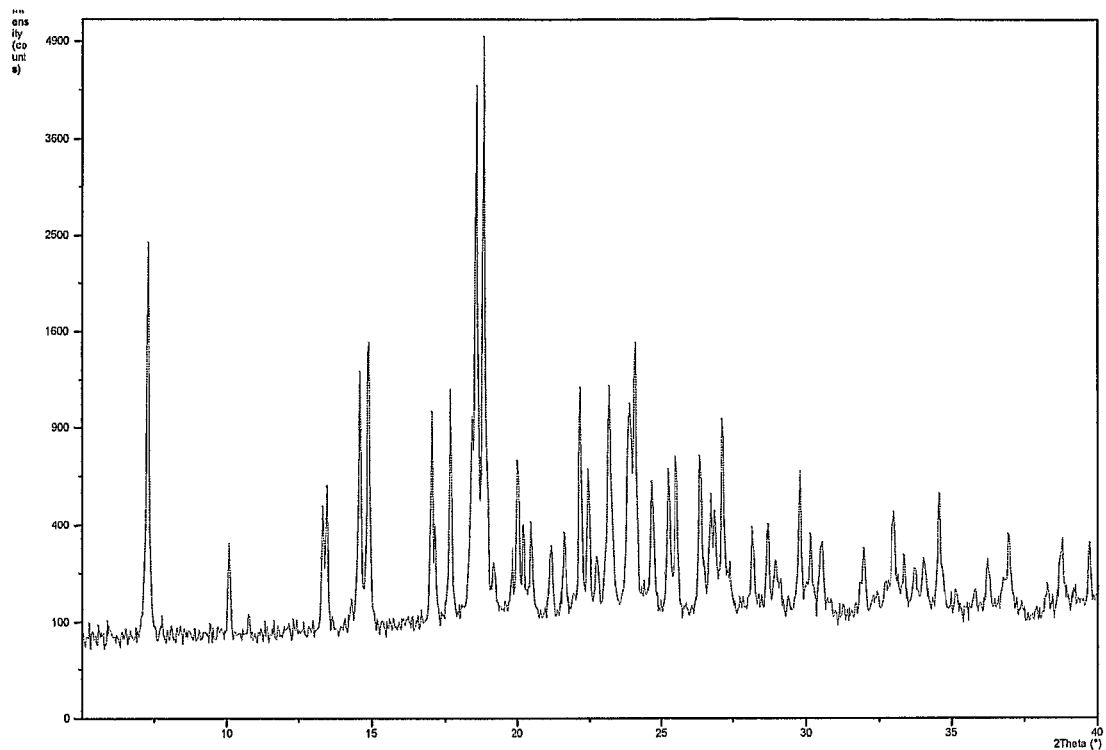
Figure 18:
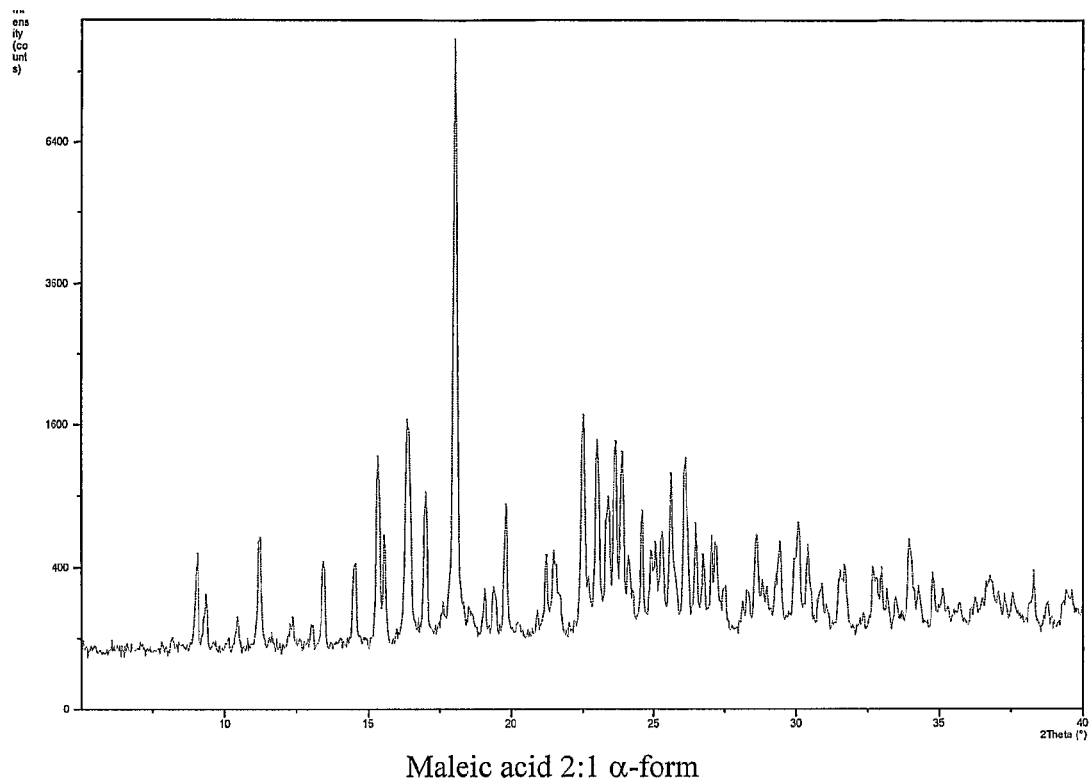
Figure 19:
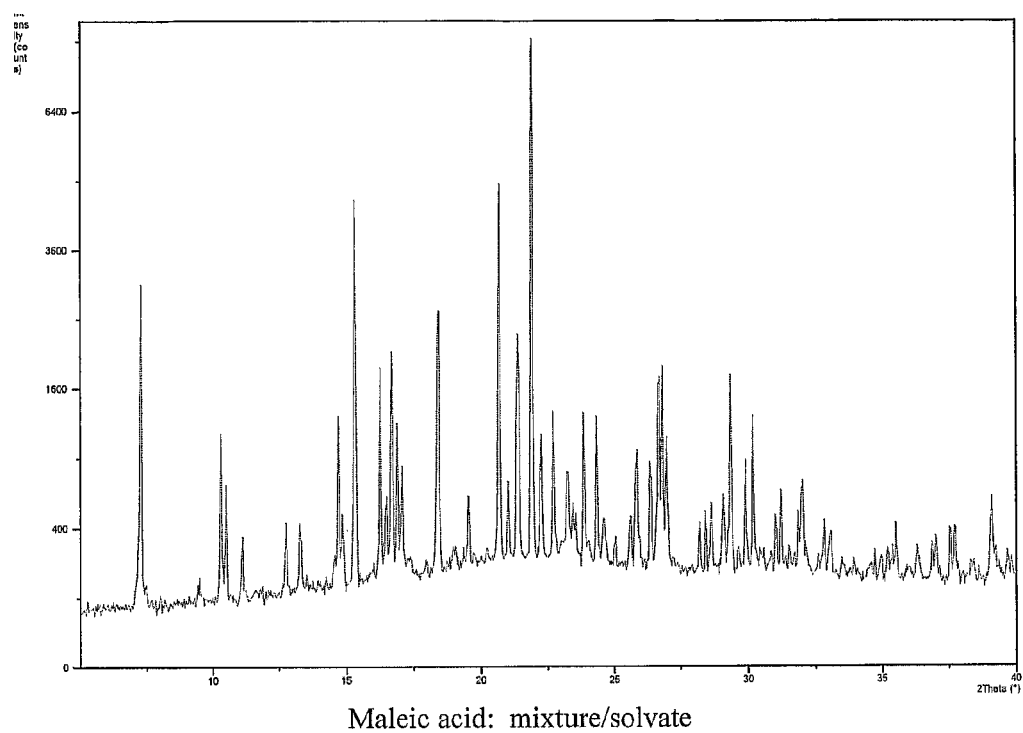
Figure 20:
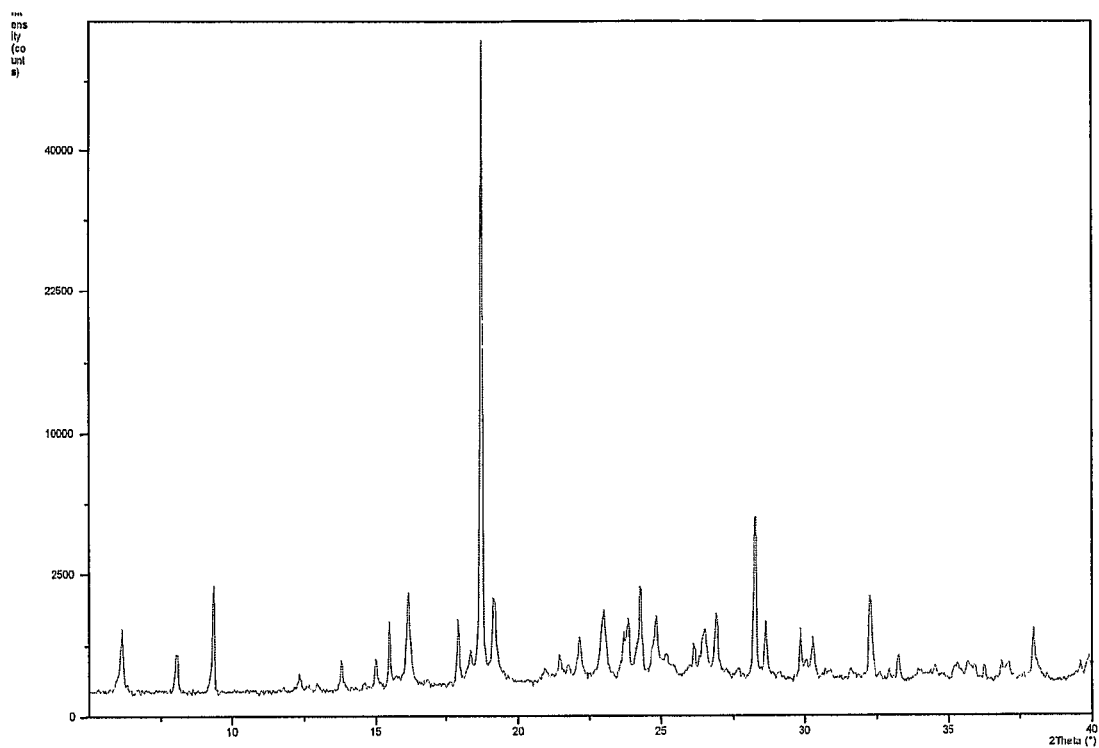
Figure 21:
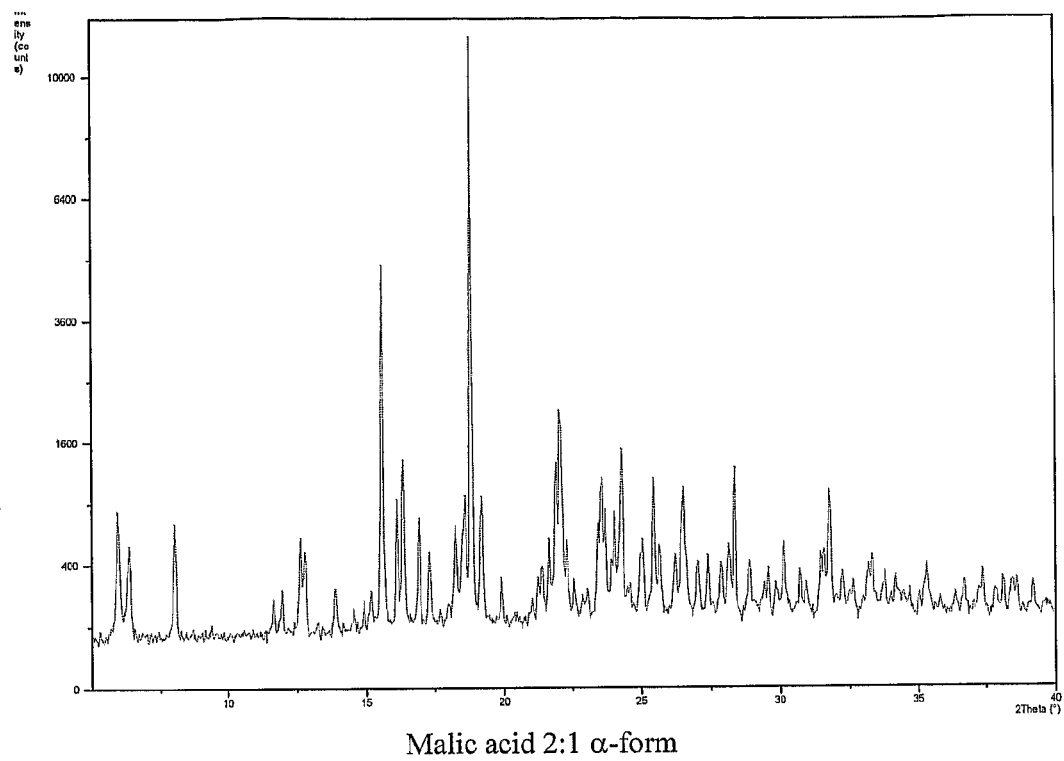
Figure 22:
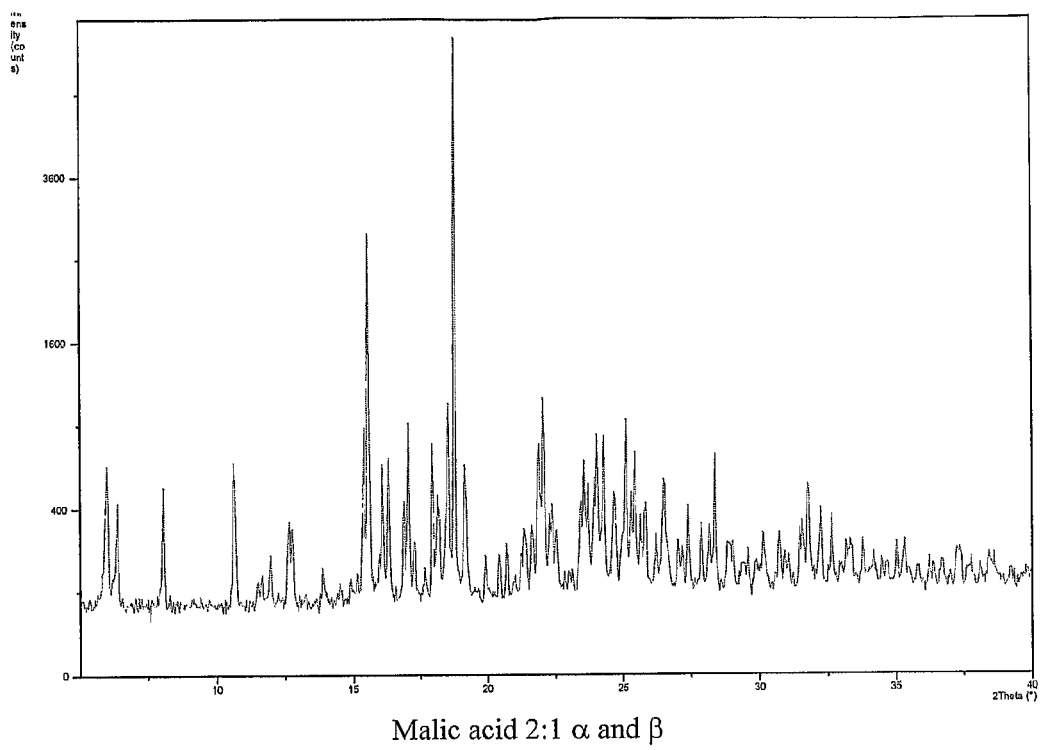
Figure 23:
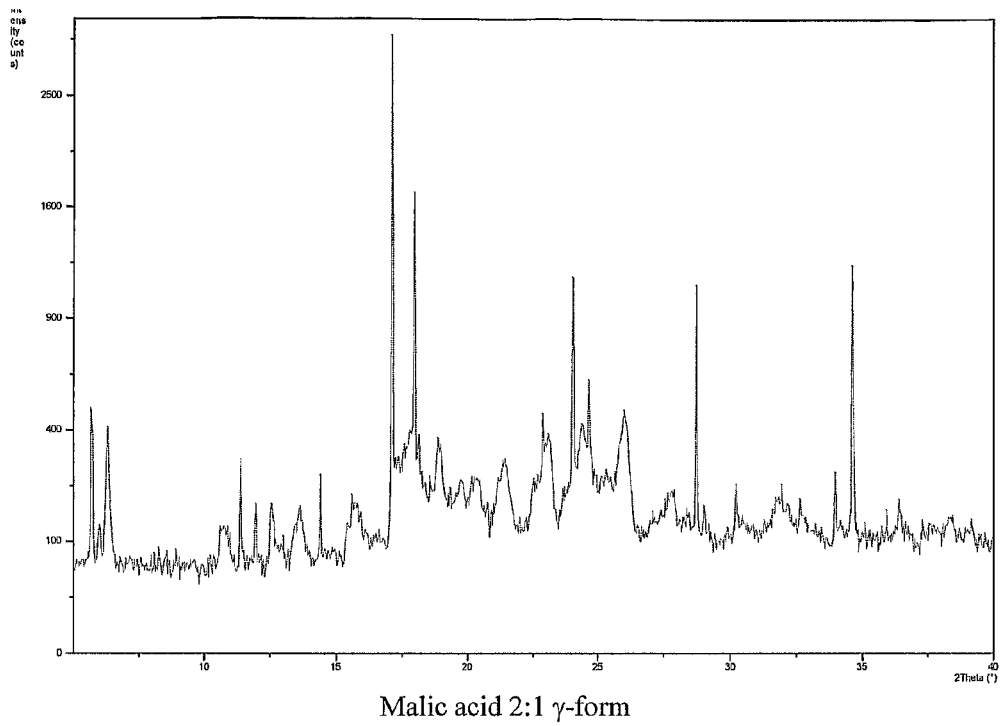
Figure 24:
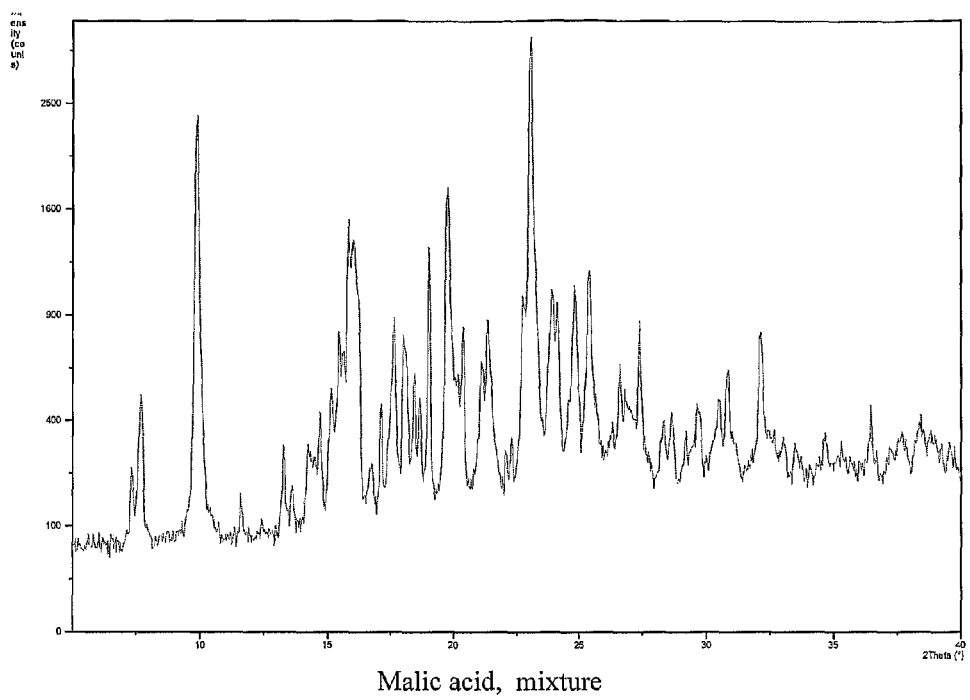
Figure 25:
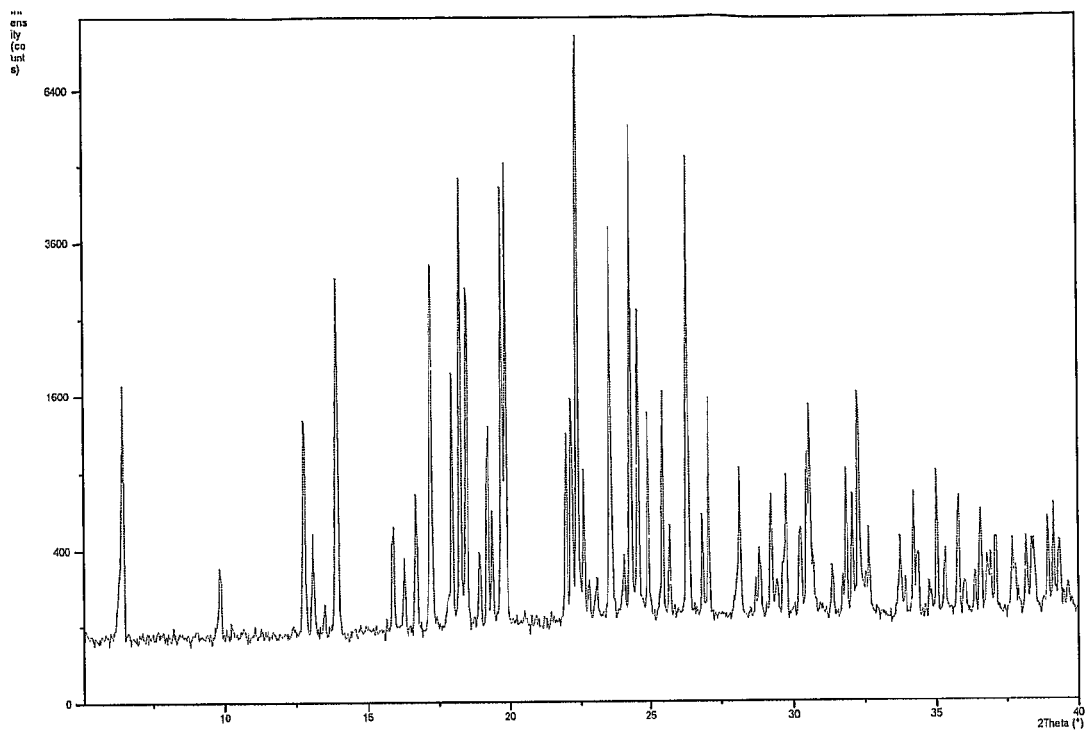
Figure 26:
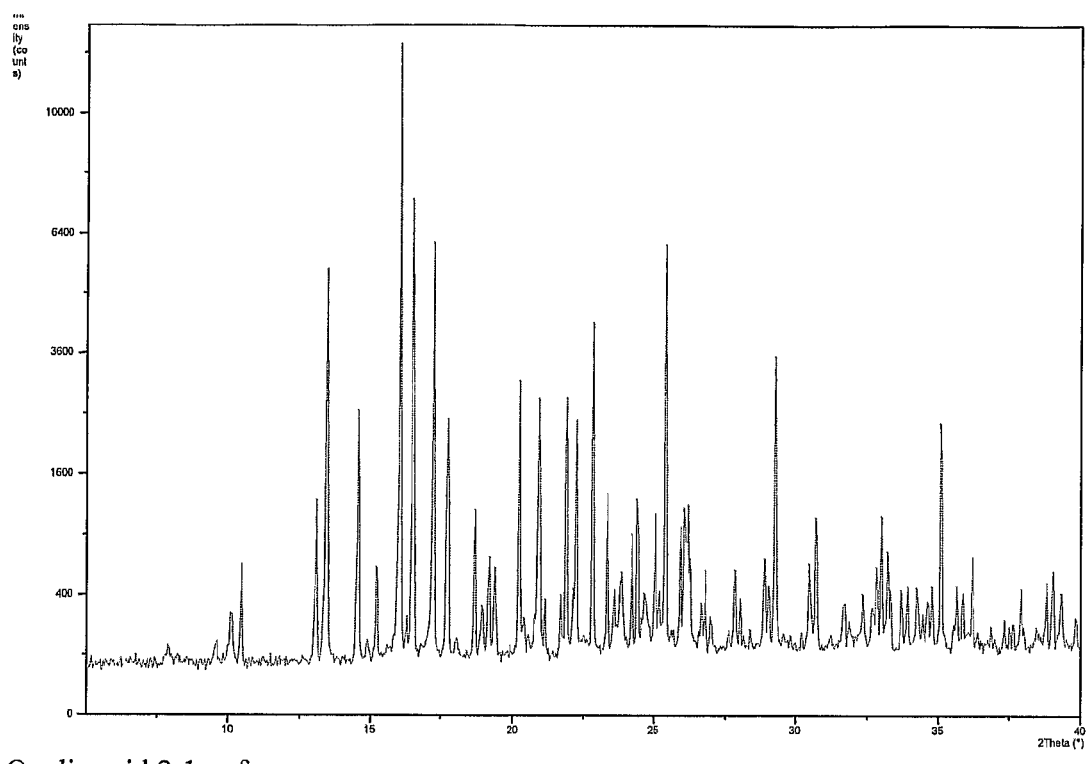
Figure 27:
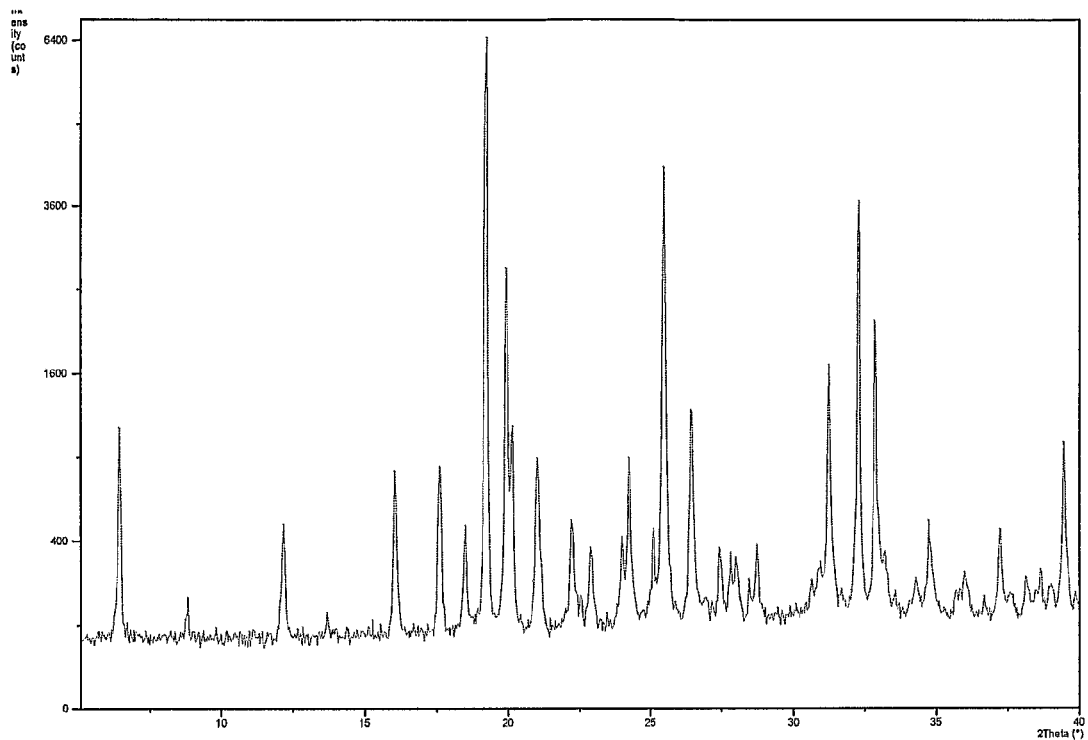
Figure 28:
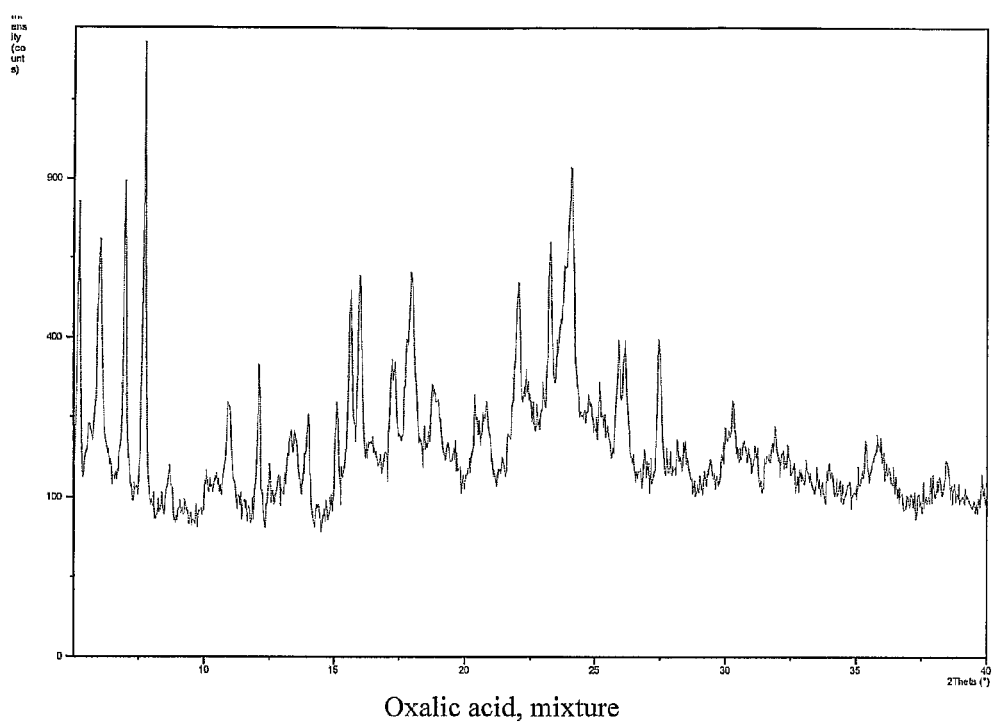
Figure 29:
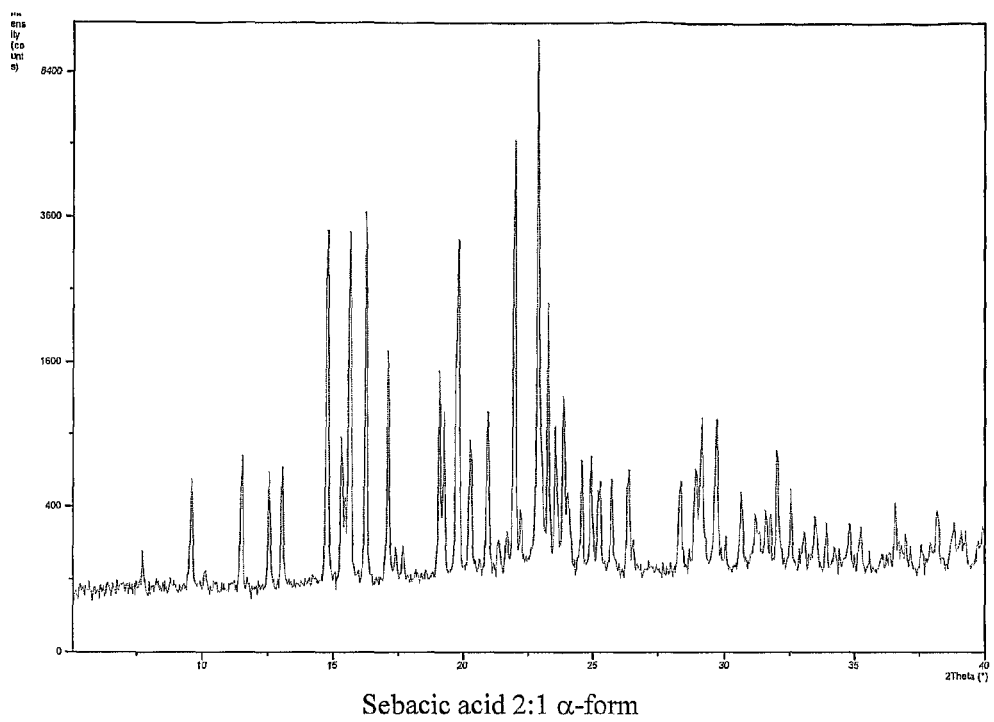
Figure 30:
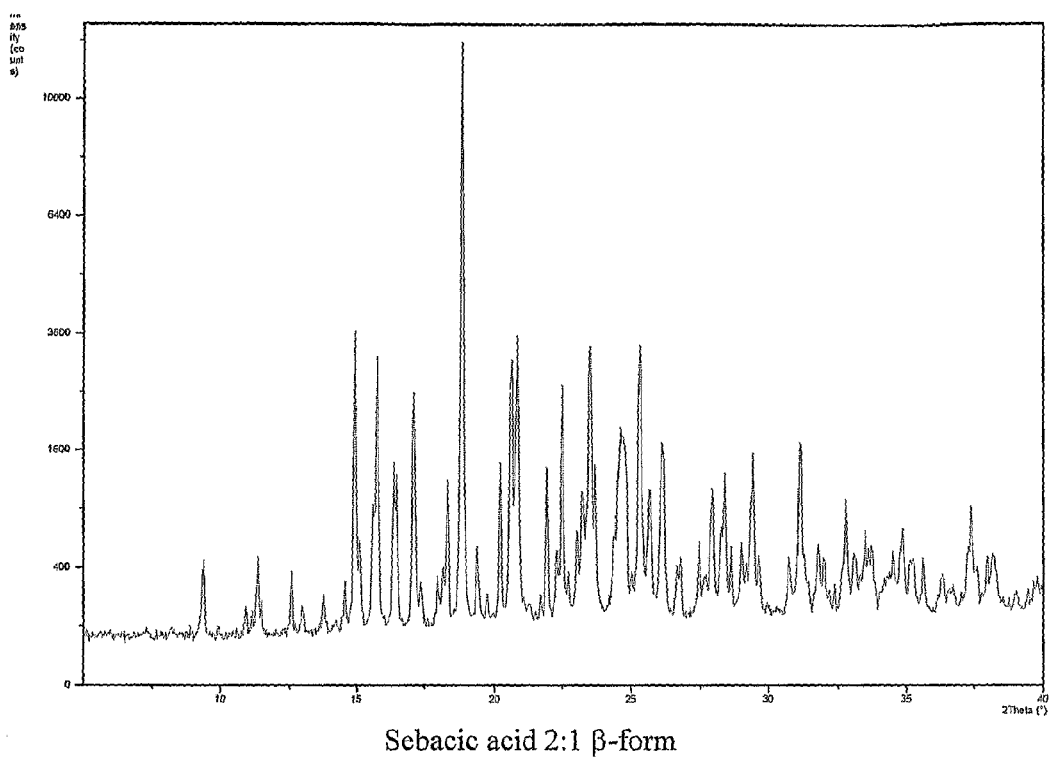
Figure 31:
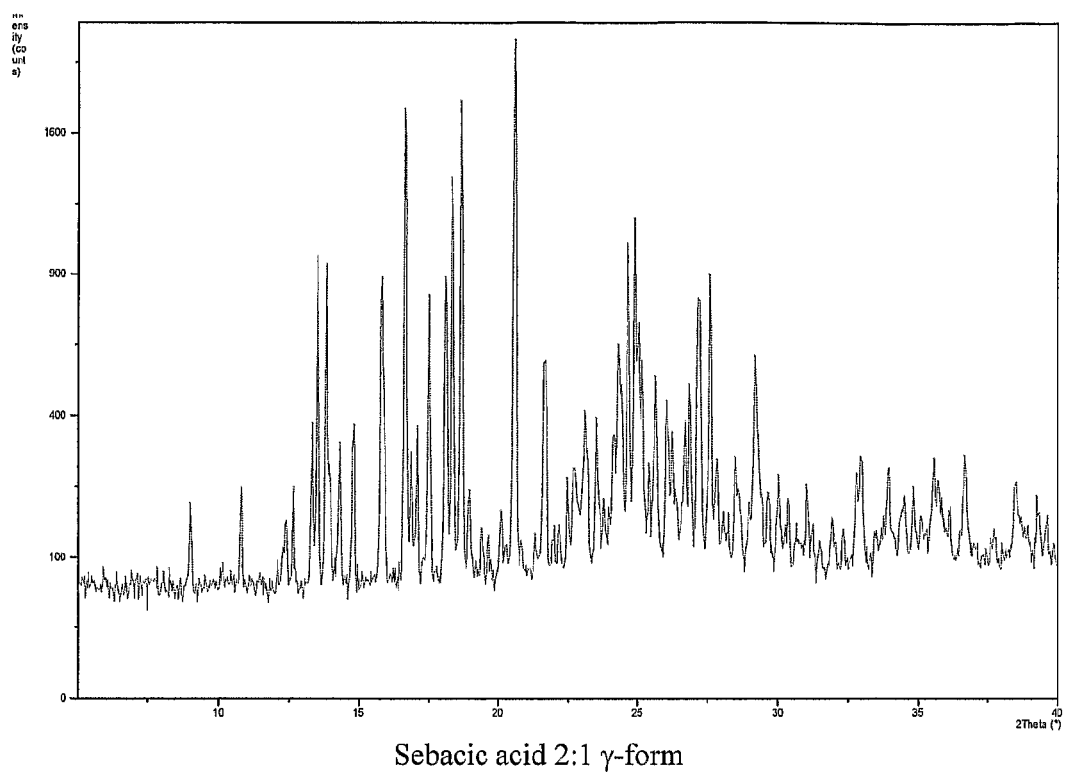
Figure 32:
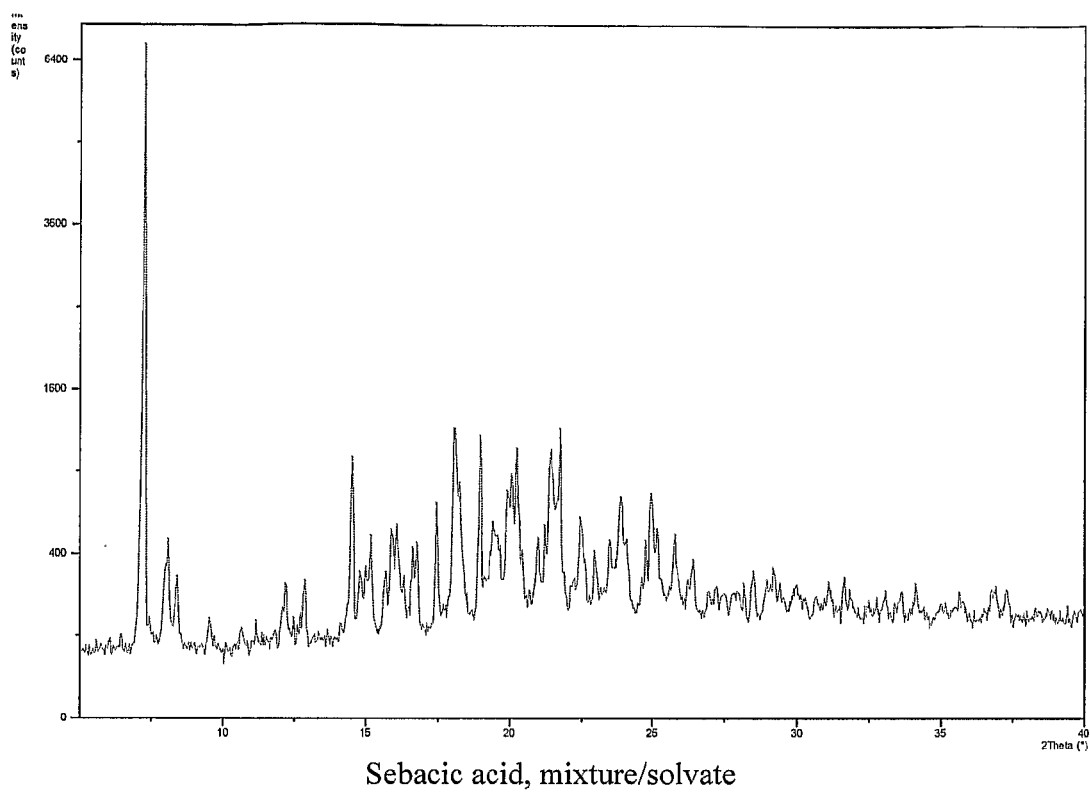
Figure 33:
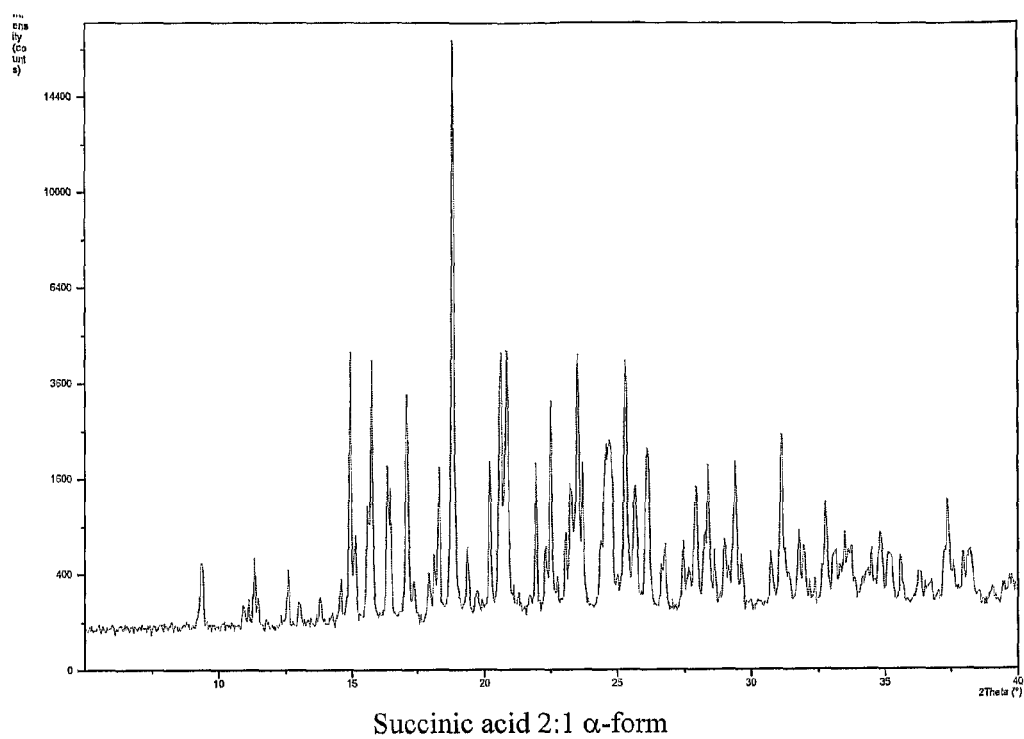
Figure 34:
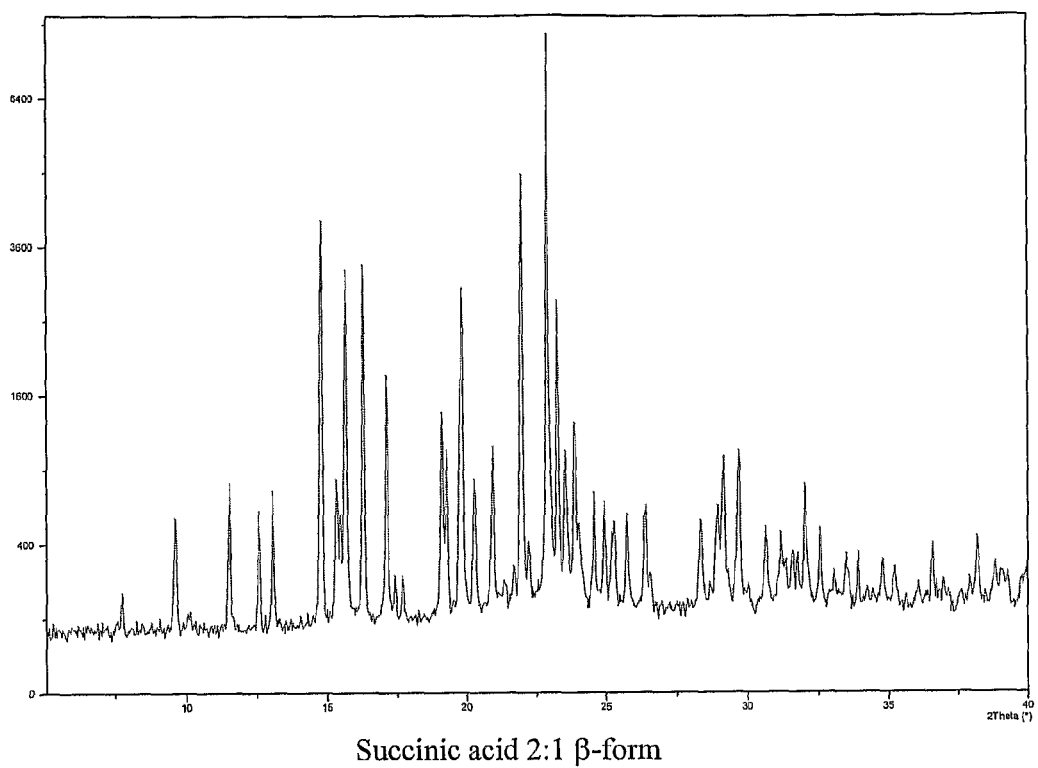
Figure 35:
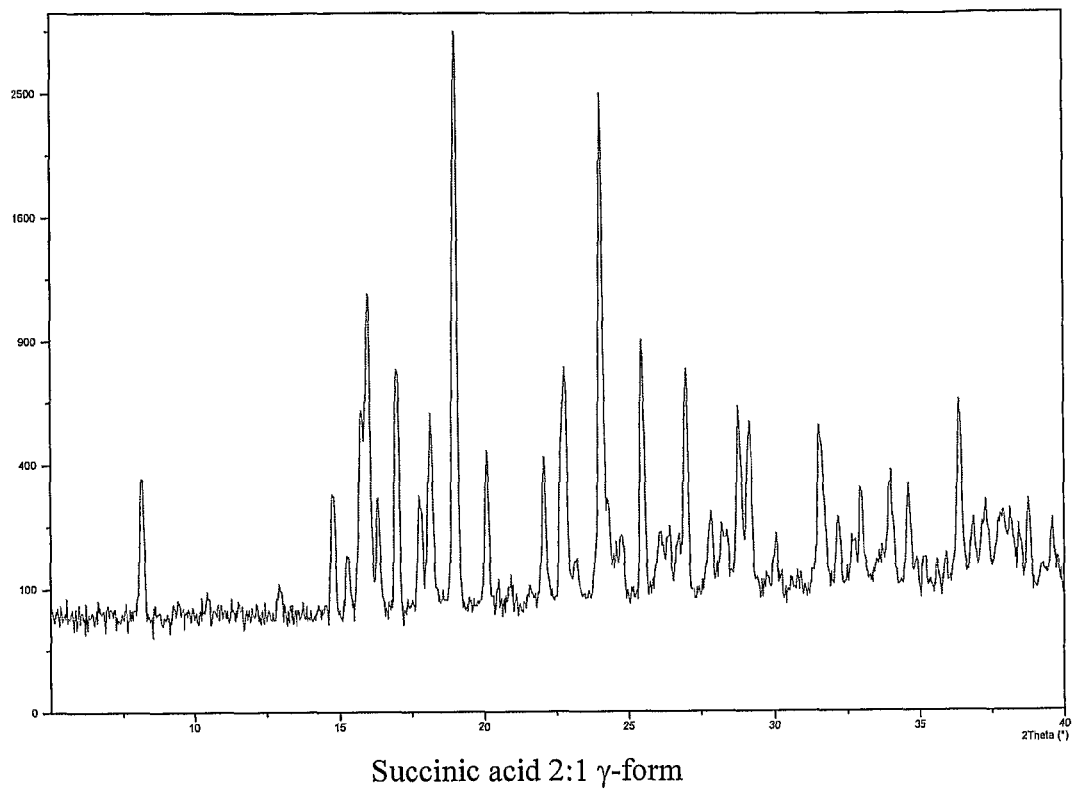
Figure 36:
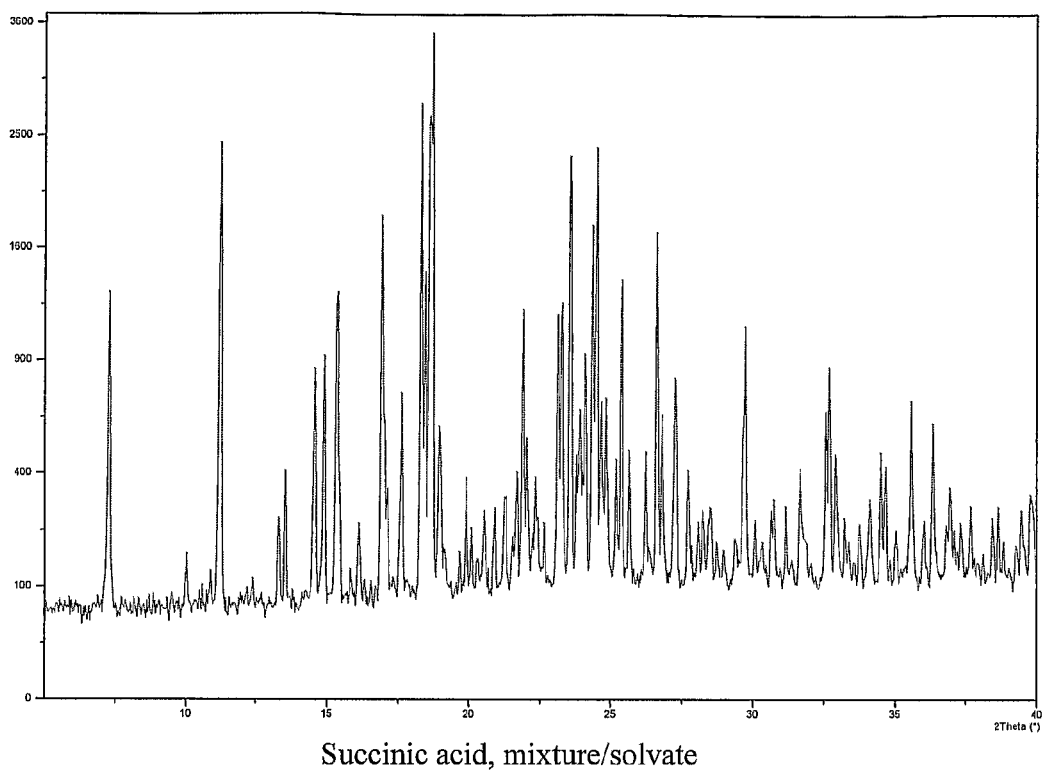
Figure 37:
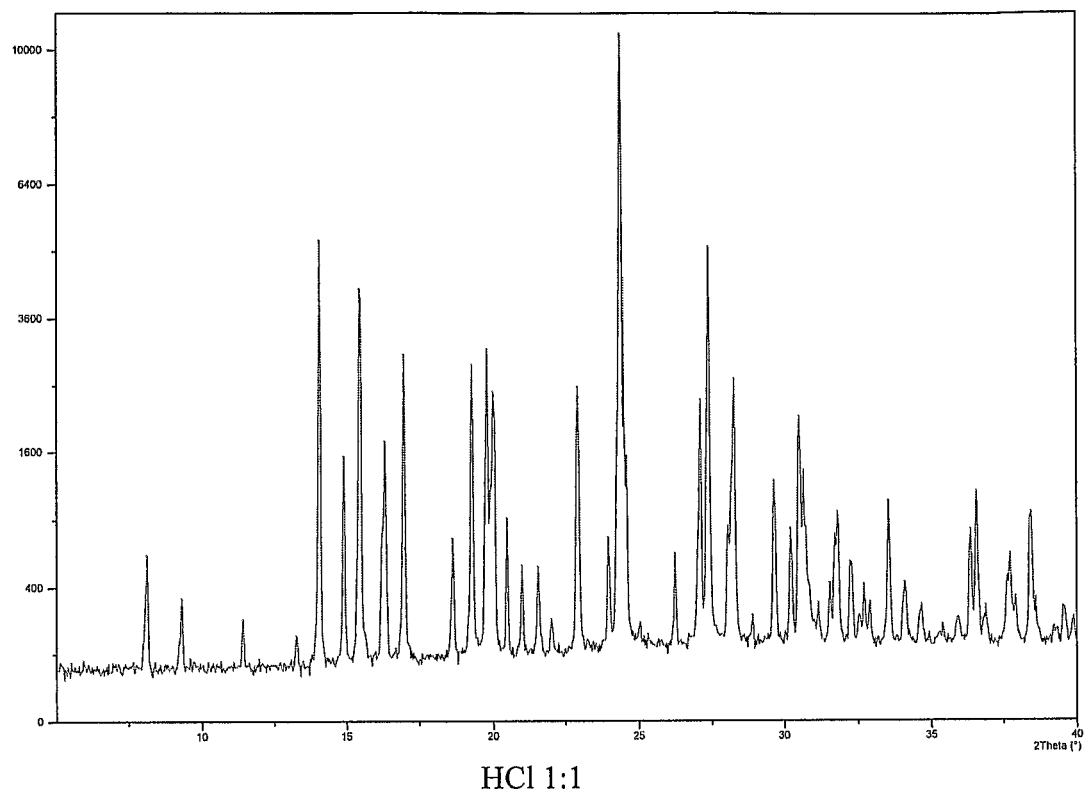
Figure 38:
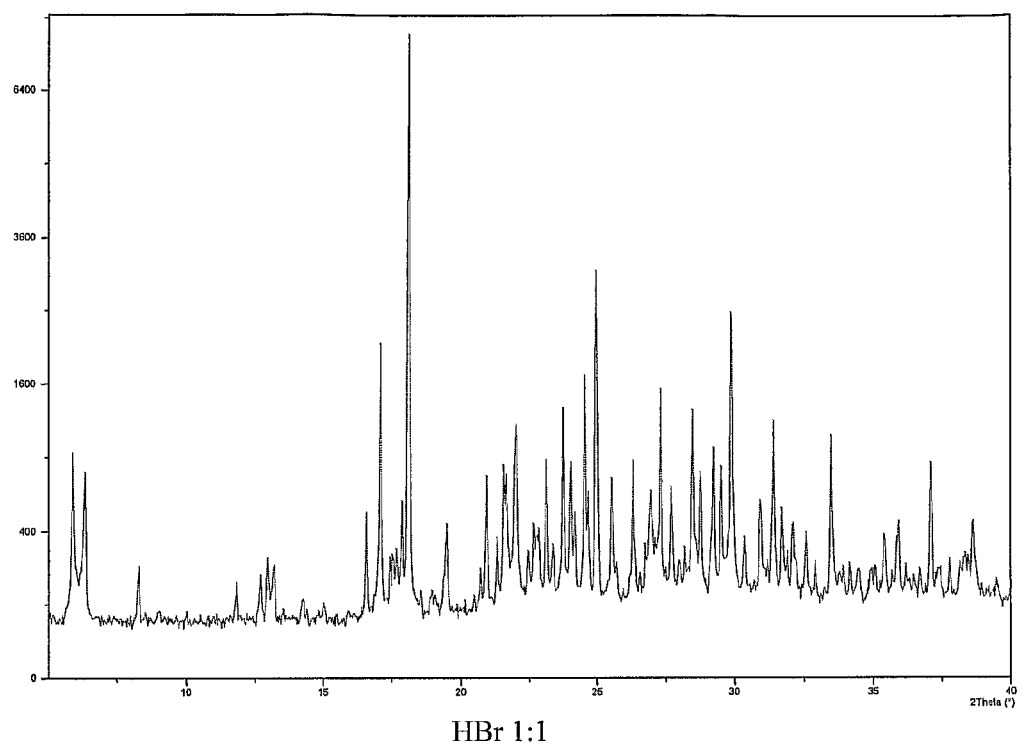
Figure 39:
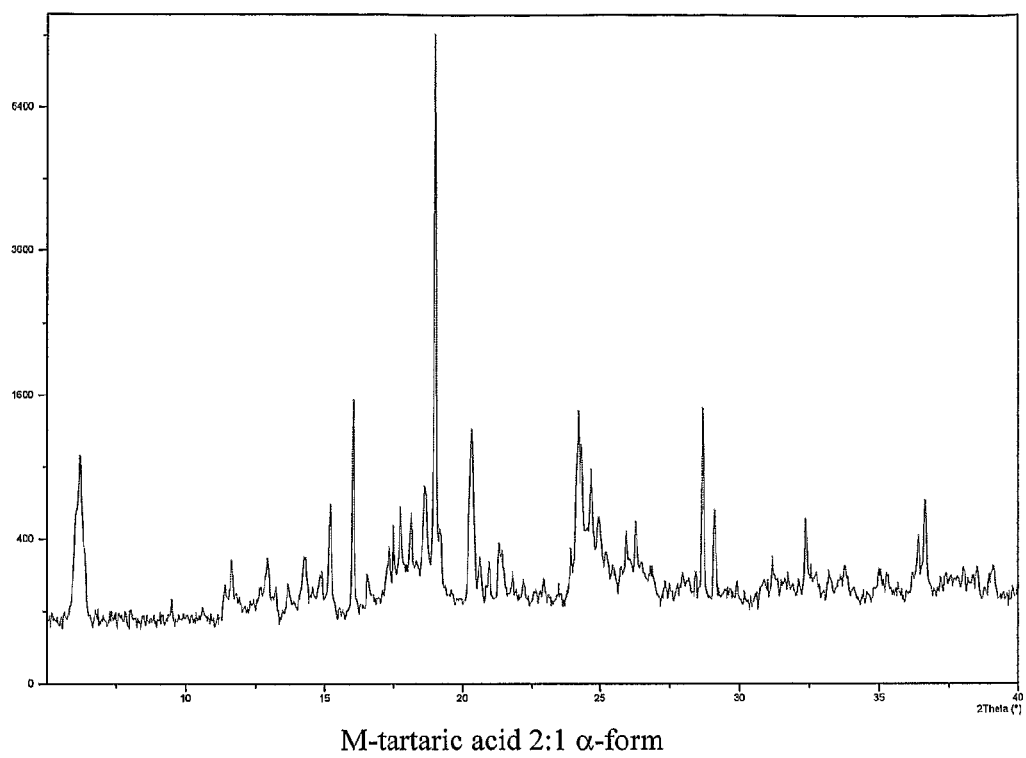
Figure 40:
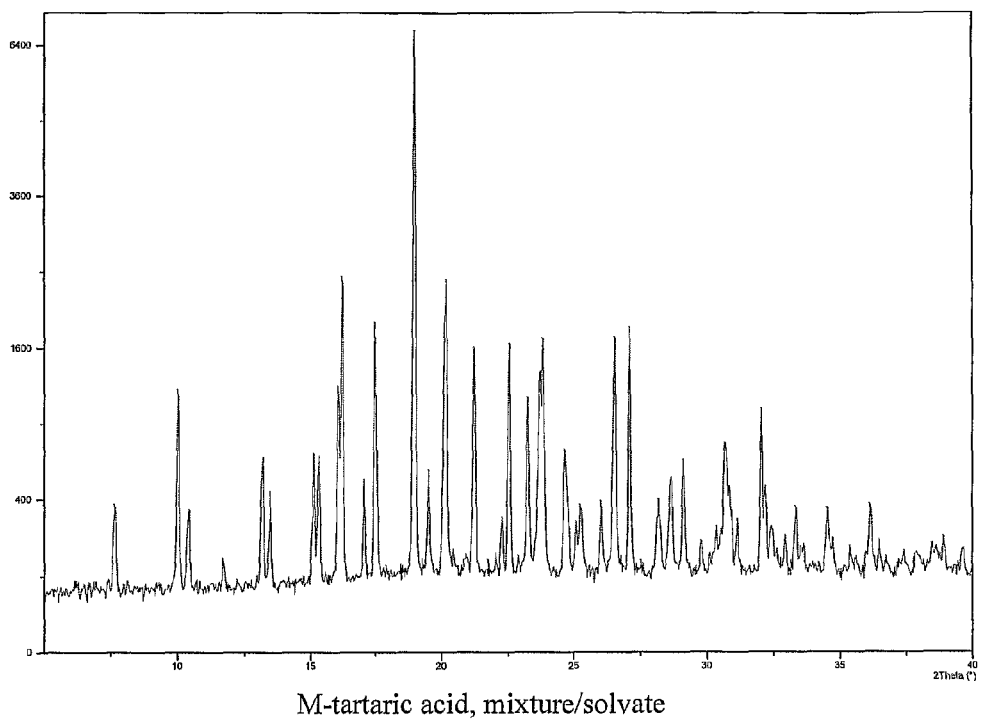
Figure 41:
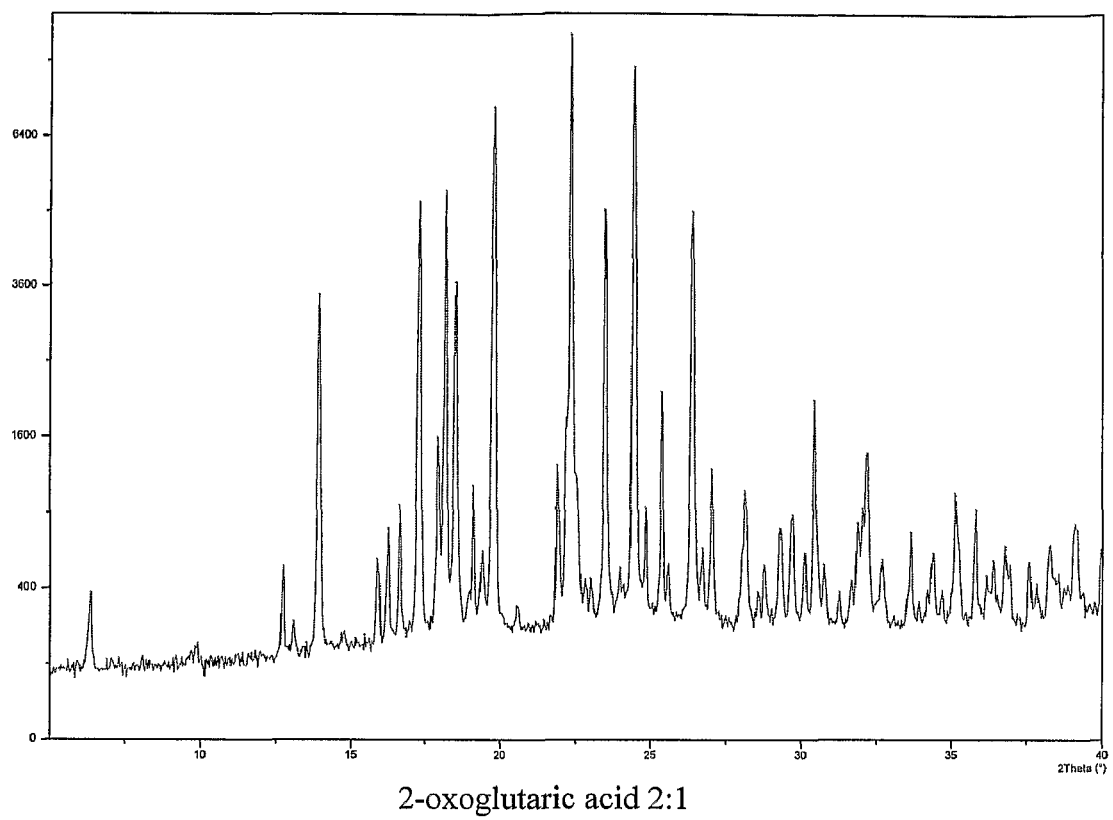
Figure 42:
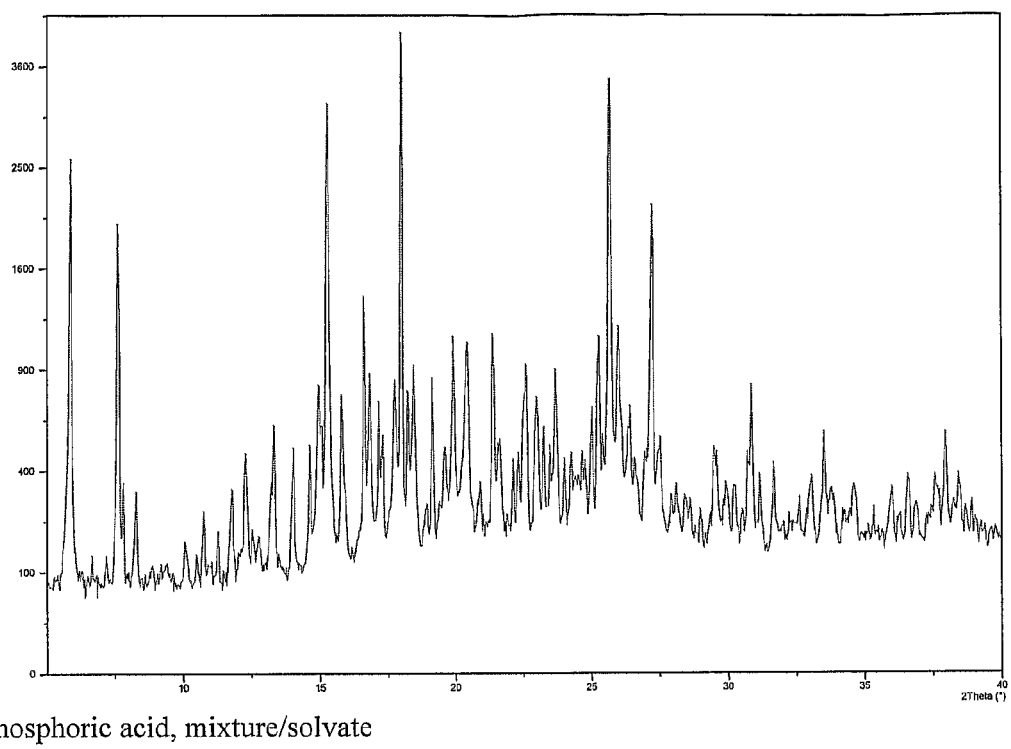
Figure 43:
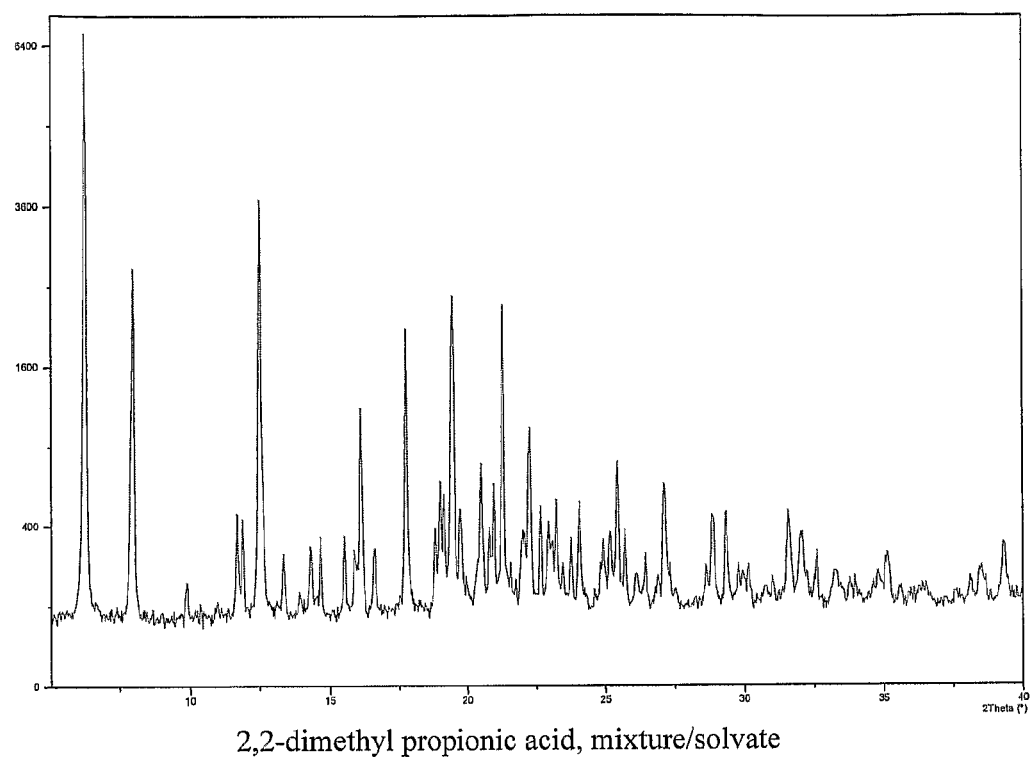
Figure 44:
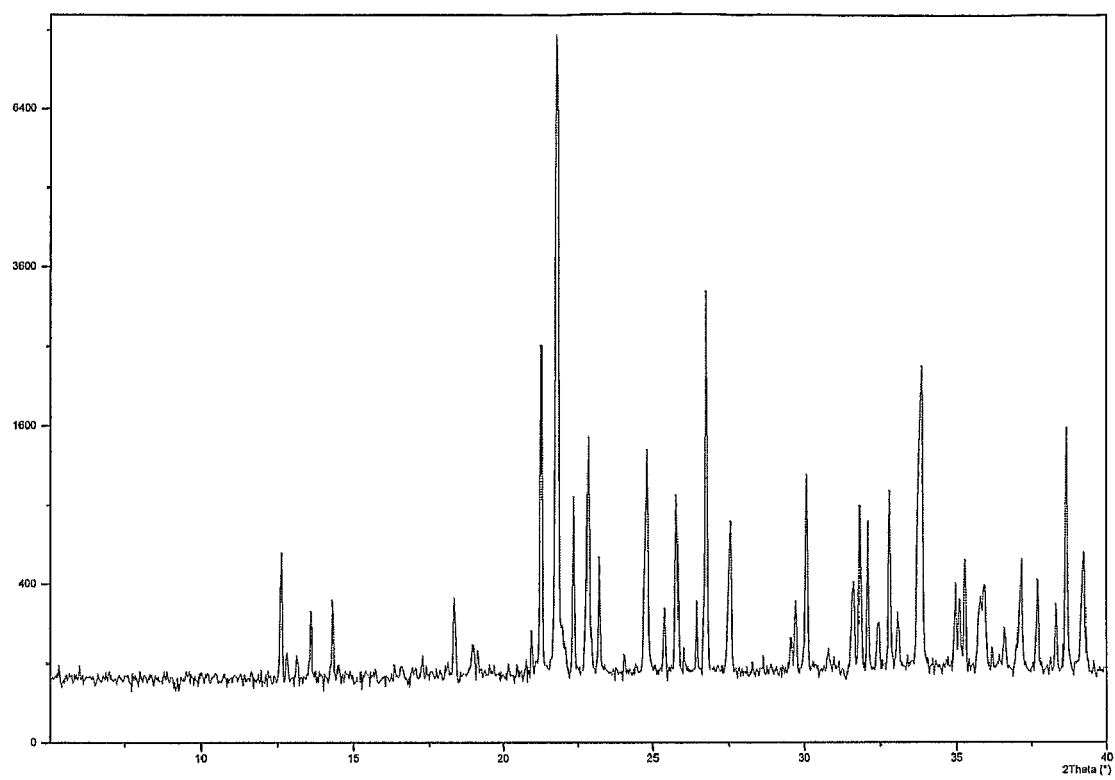

FIG. 1: X-ray powder diffractogram of the α form of the L(+) hydrogen tatrate salt
FIG. 2: X-ray powder diffractogram of the β form of the L(+) hydrogen tatrate salt
FIG. 3: Effect of compounds of the present invention on sensitised amphetamine response in mice
FIG. 4: Effect of compounds of the present invention on amphetamine chlordiazepoxide induced hyperactivity
FIG. 5: Effect of compounds of the presents invention on mouse marble burying
FIG. 6: Effects of compounds of the present invention on stress-induced hyperthermia
FIG. 7: XRPD Acetic acid salt 1:1 α-form
FIG. 8: XRPD Acetic acid salt 1:1 β-form
FIG. 9: XRPD propionic acid salt 1:1
FIG. 10: XRPB 2-hydroxy isobutyric acid salt 1:1
FIG. 11: XRPD adopic acid salt 2:1 α+β-form
FIG. 12: XRPD adipic acid salt 2:1 β-form
FIG. 13: XRPD adipic acid salt 2:1 γ-form
FIG. 14: XRPD fumaric acid salt 2:1 α+β-form
FIG. 15: XRPD fumaric acid salt 2:1 α-form
FIG. 16: XRPD fumaric acid salt 2:1 γ-form
FIG. 17: XRPD fumaric acid salt mixture/solvate
FIG. 18: XRPD maleic acid salt 2:1 α-form
FIG. 19: XRPD maleic acid mixture/solvate
FIG. 20: XRPD malonic acid salt 2:1 α-form
FIG. 21: XRPD Malic acid salt α-form
FIG. 22: XRPD malic acid salt 2:1α+β-form
FIG. 23: XRPD malic acid salt 2:1 γ-form
FIG. 24: XRPD malic acid salt mixture
FIG. 25: XRPD glutaric acid salt 2:1 α-form
FIG. 26: XRPD oxalic acid salt 2:1 α-form
FIG. 27: XRPD oxalic acid salt 2:1 β-form
FIG. 28: oxalic acid salt mixture
FIG. 29: sebacic acid salt 2:1 α-form
FIG. 30: XRPD sebacic acid salt β-form
FIG. 31: XRPD sebacic acid salt 2:1 γ-form
FIG. 32: XRPD sebacic acid salt mixture/solvent
FIG. 33: XRPD succinic acid salt 2:1 α-form
FIG. 34: XRPD succinic acid salt 2:1 β-form
FIG. 35: XRPD succinic acid salt γ-form
FIG. 36: XRPD succinic acid salt mixture/solvate
FIG. 37: XRPD hydrochloric acid salt 1:1 α-form
FIG. 38: XRPD hydrobromic acid salt α-form
FIG. 39: XRPD meso-tataric acid salt 2:1 α-form
FIG. 40: XRPD meso-tataric acid salt mixture/solvate
FIG. 41: XRPD 2-oxoglutaric acid 2:1 salt α-form
FIG. 42: XRPD phosphoric acid salt mixture/solvate
FIG. 43: XRPD 2,2-dimethyl propionic salt acid mixture/solvate
FIG. 44: XRPD glutaminic acid salt mixture/solvate

DETAILED DESCRIPTION OF THE INVENTION

Sleep patterns vary widely from person to person and also during the life span of an individual. Typically, an adult sleeps 7-8 hours a night, whereas some needs 10-12 hours and others again can make do with 4-5 hours. The amount and the quality of the sleep should be sufficient for the sleeper to feel rested, refreshed, and able to perform the next day's activity adequately.

Sleep quality may be quantified subjectively, i.e. the subject at interest scores himself or is being scored on relevant parameters describing how the sleep is perceived. Clinical scores used include HAS, HRSD and the Pittsburgh Sleep Quality Index. Alternatively, objective information may be obtained by measuring brain activity (electroencephalography, EEG), muscle activity (electromyography, EMG), or observing physiological parameters, such as eye movement. Using objective quantification of sleep, two types of sleep, i.e. REM and non-REM sleep have been defined in mammals, and indeed in humans. REM (Rapid Eye Movement) sleep is defined by fast and low voltage brain waves (as measured by EEG) similar to the awake state, and irregular autonomic activities, such as heart rate and respiration. This type of sleep is associated with rapid horizontal eye movements, involuntary muscle jerks and dreaming. Non-REM sleep, on the other hand, is defined by slow and high voltage brain waves and the autonomic activities, such as heart rate and blood pressure, being low and regular. Non-REM sleep is a deep and dreamless type of sleep. It is thought that certain restorative processes take place during the non-REM sleep, for instance growth hormone is being released during this type of sleep.

When EEG is obtained from a sleeping subject a pattern of sleep consisting of five different stages emerge, four non-REM stages and one REM stage. Stage 1 shows a slowing of EEG activities and is the transition from drowsiness to light sleep. Stage 2 shows an emergence of sleep spindles and K-complex wave forms. Stage 3 and 4 are characterised by slow waves and are of deep sleep. Stage 5 is the REM sleep. Stage 3 and stage 4 are often referred to as slow wave sleep or SWS. During the night, individuals progress from the waking state to stage 1 (sleep latency) and slowly through stages 2 to 4. The individual then enters an episode of REM sleep followed by re-progression through stages 1-4. The pattern varies from person to person, but typically consists of 4-5 cycles during the night. The cycles change in the course of the night, so that most of the deep sleep (stages 3 and 4) takes place during the first half of the night and most of the REM sleep takes place in the second half of the night. Overall, the average adult will experience that 80% of the sleep is non-REM sleep and 20% of the sleep is REM sleep. The patterns of occurrences of the various stages of sleep during the night is referred to as the sleep architecture.

An improvement of sleep or a lack of adverse sleep effects associated with a therapeutic intervention is ultimately judged by how the sleep quality is perceived by the patient. Typically, parameters such as sleep latency (time before sleep occurs), number of awakenings during the night, sleep latency if awakened, the feeling of being rested and refreshed in the morning, insomnia, sleep duration, sleep sufficiency, early morning awakening, next day performance, and excessive daytime sleepiness are important for how an individual perceives his sleep. Some of these parameter may be assessed more objectively by measuring EEG or EMG as discussed above.

As shown in the examples, compounds of the present invention increase the amount of slow wave sleep, decreases the amount of REM sleep and decrease the sleep latency in a dose dependent manner in rats. These pre-clinical finding are expected to translate into improved sleep quality for patients who are being administered said compounds. As compounds having a combined inhibitory effect on the serotonin and noradrenaline uptake would prima facia be expected to reduce sleep quality, this is an unexpected result.

Increased blood pressure may give rise to dizziness and drowsiness, but often a subject suffering form increased blood pressure is not aware of his situation because there are no immediate or severe symptoms. Nevertheless, it is important to avoid even slightly increased blood pressure as it is likely to have consequences, such as myocardial infarct, heart insufficiency, renal insufficiency and cerebral hemorrhage, in the long term.

Blood pressure is normally stated as the diastolic and the systolic blood pressure. The systolic blood pressure is the pressure when the heart is fully contracted whereas the diastolic blood pressure is the pressure when the heart is fully relaxed. Blood pressure is typically measured rested and supine, i.e. when the subject is lying down. The average healthy subject will have a diastolic/systolic blood pressure of 80-90/130-140 mm Hg.

The data shown in the examples show that compounds of the present invention gives rise to a decrease in the blood pressure in dogs. This pre-clinical finding is expected to translate into little or no blood pressure increase, perhaps a slight decrease in the blood pressure in a clinical setting. This is an unexpected result as compounds having noradrenalin reuptake inhibiting effect would prima facia be expected to give rise to an increase in the blood pressure.

Bipolar disorder was formerly known as manic-depressive illness and it is characterised by recurrent episodes of mania and depression. A major challenge in the treatment in the treatment of bipolar depression (or the depression associated with bipolar disease) is to avoid the manic shift, i.e. avoid that depressed patients develop manic episodes as a consequence of the anti-depressive treatment. Treatment—emergent mania has been reported for a significant fraction of patients with bipolar depression after treatment with anti-depressants [*J. Clin. Psych.*, 67, suppl 11, 18-21, 2006]. Typically manic episodes are treated with antipsychotics, such as quetiapine or olanzapine, both of which exhibit $5\text{-HT}_{2A}$ antagonistic effects or with lithium. A compound combining serotonin reuptake inhibition with antagonistic effect on the $5\text{-HT}_{2A}$ receptor would thus seem to be the ideal compound for the treatment of bipolar depression avoiding a manic shift. As shown in examples 12 and 13, the compounds of the present invention show antimanic effect which in the combination with the antipressive properties suggest a use in the treatment of bipolar depression.

Sleep disturbances and anxiety are hallmarks of post traumatic stress disorder (PTSD). As discussed elsewhere, the $5\text{-HT}_{2A}$ antagonistic effect of compounds of the present invention provides improvements of the sleep quality. Moreover, clinical experience with prazosin, an $\alpha_1$ receptor antagonist, in the treatment of military veterans suffering from PTSD shows that $\alpha_1$ receptor antagonists can reduce traumatic nightmares and improve sleep quality [*Biol Psychia.* 61, 928-934, 2007]. As shown in the experiments reported in Example 14, compounds of the present invention show strong anxiolytic properties. Consequently, the compounds of the present invention combining effect on sleep quality and anxiety are useful in the treatment of PTSD.

Melancholia is a particular subtype of depression often connected to severe depression; this type of depression is also referred to as melancholic depression. Melancholia is associated with anxiety, dread of the future, insomnia, and loss of appetite. Compounds that inhibit both the serotonin and the norepinephrine reuptake, such as e.g. venlafaxine, have been shown to be particular effective in the treatment of patients with severe depression and melancholia [*Depres. Anxiety*, 12, 50-54, 2000]. Additionally, the α-1 adrenergic receptor and $5\text{-HT}_{2A}$ antagonism of the compounds of the present invention is expected to help normalise sleep, wherefore said compounds are useful in the treatment of melancholia.

Hot flushes are a symptom associated with the menopausal transition. Some women may suffer from this to an extent where it interferes with sleep or activities in general, and where treatment is necessary. Hormone replacement therapy with oestrogen has been established practice for decades, however, recently concerns have been voiced on side effects, such as breast cancer and cardiac events. Clinical trials with SSRIs have shown that these compounds have an effect on hot flushes, albeit less than for oestrogen [*J. Am. Med. Ass.*, 295, 2057-2071, 2006]. Treatment of hot flushes with compounds inhibiting serotonin reuptake, e.g. compounds of the present invention could, however, be an alternative treatment for women who can not or will not accept oestrogen.

In one embodiment, the invention relates compound I, which is [2-(6-fluoro-1H-indol-3-ylsulfanyl)benzyl]methyl amine

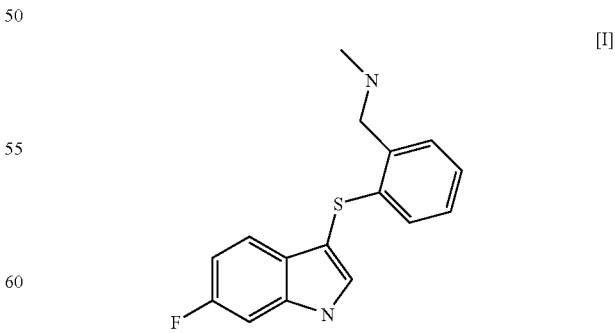

[I]

and pharmaceutically acceptable salts thereof, provided said compound is not the free base in a non-crystalline form.

In one embodiment, said pharmaceutically acceptable salts are acid addition salts of acids that are non-toxic. Said salts include salts made from organic acids, such as sabaconic, 2-hydroxy isobutyric, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic salts, such as hydrochloric, hydrobromic, sulfuric, sulfamic, phosphoric and nitric acids. Particular mentioning is made of salts made from methanesulfonic acid, maleic acid, fumaric acid, mesotartaric acid, (+)-tartaric acid, (−)-tartaric acid, hydrochloric acid, hydrobromic acid, sulphuric acid, phosphorous acid and nitric acid. Distinct mentioning is made of the L-(+)-hydrogen tatrate salt. Additional salts are mentioned in the examples.

Oral dosage forms, and in particular tablets or capsules, are often preferred by the patients and the medical practitioner due to the ease of administration and the consequent better compliance. For tablets and capsules, it is preferable that the active ingredients are crystalline. In one embodiment, the compounds of the present invention are crystalline.

In one embodiment the crystals of the present invention are solvates, i.e. crystals wherein solvent molecules form part of the crystal structure. The solvate may be formed from water, in which case the solvates are often referred to as hydrates. Alternatively, the solvates may be formed from other solvents, such as e.g. ethanol, acetone, or ethyl acetate. The exact amount of solvate often depends on the conditions. For instance, hydrates will typically loose water as the temperature is increased or as the relative humidity is decreased.

In one embodiment, the compounds of the present invention are not solvates.

For oral dosage forms using crystalline active ingredients it is also beneficial if said crystals are well-defined. In the present context, the term "well-defined" in particular means that the stoichiometry is well-defined, i.e. that the ratio between the ions forming the salt is the ratio between small integers, such as 1:1, 1:2, 2:1, 1:1:1, etc. In one embodiment, the compounds of the present invention are well-defined crystals.

Some compounds may be hygroscopic, i.e. absorb water when exposed to humidity. Hygroscopicity is generally regarded as an undesired property for compounds that are to be presented in a pharmaceutical formulation, in particular in a dry formulation, such as tablets or capsules. In one embodiment, the invention provides crystals with low hygroscopicity.

The solubility of an active ingredient is also of significance for the choice of dosage form as it may have a direct impact on bio-availability. For oral dosage forms, a higher solubility of the active ingredient is generally believed to be beneficial as it increases the bio-availability. Some patients, e.g. elderly patients may have difficulties swallowing tablets, and oral drop solutions may be a suitable alternative avoiding the need for swallowing tablets. In order to limit the volume of an oral drop solution, it is necessary to have a high concentration of the active ingredient in the solution, which again requires a high solubility of the compound. It has been found that acid addition salts from 2-hydroxy isobutyric acid, hydrochloric acid and hydrobromic acid forms well-defined 1:1 salts with a relatively high solubility.

Figure 2:
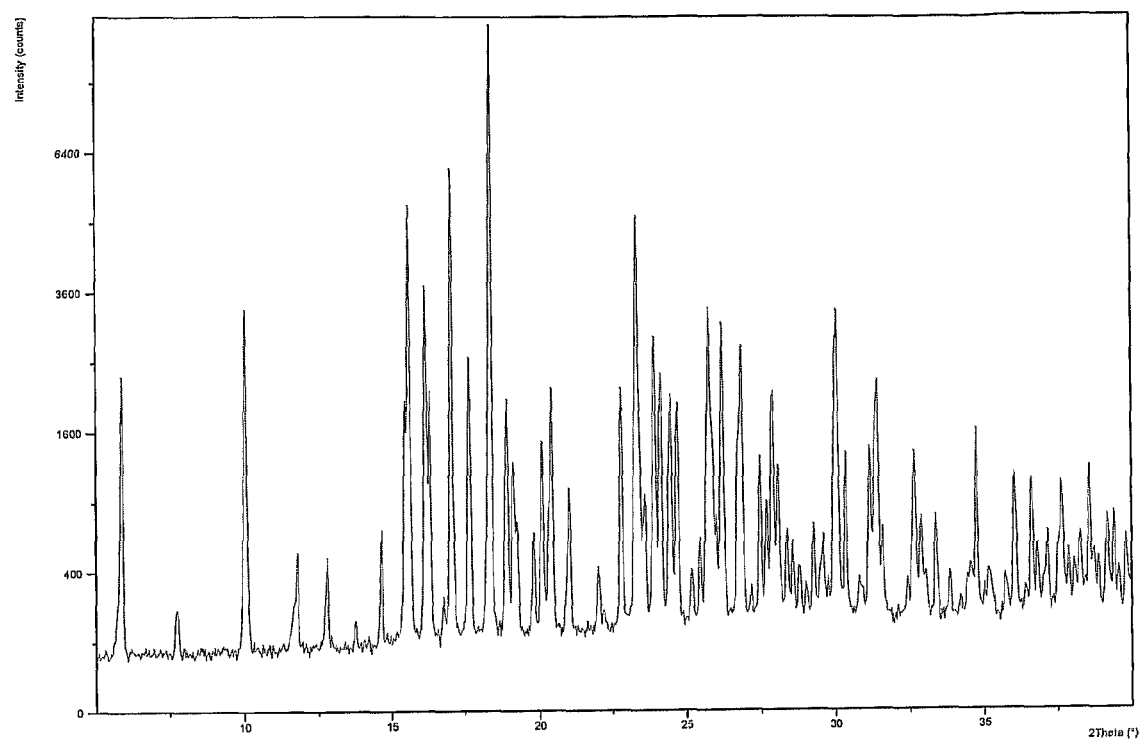

The crystalline compounds of the present invention may exist in more than one form, i.e. they may exist in polymorphic forms. Polymorphic forms exist if a compound can crystallize in more than one form. The present invention is intended to encompass all such polymorphic forms, either as pure compounds or as mixtures thereof. In one embodiment, the invention provides crystalline salts of [2-(6-fluoro-1H-indol-3-ylsulfanyl)benzyl]methyl amine L-(+) hydrogen tatrate which exists in two polymorphic forms, the α form and the β form. The XRPD of the α form and the β form are shown in FIGS. 1 and 2, respectively. As shown in the examples below, the α form has a higher melting point and a lower solubility and is therefore expected to be a more stable form than the β form. In a particular embodiment, the invention relates to the α form of [2-(6-fluoro-1H-indol-3-ylsulfanyl)benzyl]methyl amine L-(+) hydrogen tatrate. In a particular embodiment, the invention provides crystalline forms of [2-(6-fluoro-1H-indol-3-ylsulfanyl)benzyl]methyl amine L-(+) hydrogen tatrate with an XRPD with major peaks at around 9.66, 14.53, 18.14 and 30.48 (°2θ). In a particular embodiment, the invention provides crystalline forms of [2-(6-fluoro-1H-indol-3-ylsulfanyl)benzyl]methyl amine L-(+) hydrogen tatrate with an XRPD as depicted in FIG. 1.

Due to the serotonin and noradrenalin reuptake inhibiting activity of the compounds of the present invention, they are useful for the treatment of diseases which will benefit from an increase in the serotonin and/or noradrenalin levels in the brain. The compounds of the present invention are particularly useful because they do not to give rise to further decrease in the sleep quality of the patients, and may even give rise to an improvement in said sleep quality, and because they give rise to no or only reduced cardiovascular side effects, such as blood pressure increase. Hence, in one embodiment, the invention relates to a method of treating a diseases which will benefit from an increase in the serotonin and/or noradrenalin levels in the brain, the method comprising administering a therapeutically effective amount of a compound of the present invention to a patient in need thereof. In one embodiment, said treatment is associated with little or no adverse sleep effects or an improvement of the sleep quality of the patient and/or with reduced or no cardiovascular side effects, such as increased blood pressure.

In another embodiment, the invention relates to a method of increasing the level of serotonin and/or noradrenalin in the brain of a subject, the method comprising administering a compound of the present invention to said subject.

In one embodiment, the invention provides a method for the treatment of an affective disorder, such as depressive disorders or anxiety disorders, the method comprising administering a therapeutically effective amount of a compound of the present invention to a patient in need thereof. In a further embodiment, said depressive disorder includes major depressive disorder, postnatal depression, melancholia, dysthymia, and depression associated with bipolar disorder, Alzheimer's, psychosis, Huntington's Disease, multiple sclerosis or Parkinson's. In a further embodiment, anxiety disorders includes general anxiety disorder, social anxiety disorder, post traumatic stress disorder, obsessive compulsive disorder, panic disorder, panic attacks, specific phobias, social phobia or agoraphobia.

The unique pharmacological profile also makes the compounds of the present invention useful in the treatment of burn-out/stress; pain; chronic pain, e.g. fibromyalgia, tension-type headache, neuropathic pain, overall pain, low back pain, shoulder pain, pain while awake, pain during daily activities, osteoarthritis and cancer pain; and acute stress disorder.

The invention also provides a method for the treatment of ADHD, hot flushes and stress urinary incontinence, the method comprising the administration of a therapeutically effective amount of a compound of the present invention to a patient in need thereof.

In one embodiment, the patient to be treated has been diagnosed with said disease.

In one embodiment, the patient to be treated suffers from or experiences inadequate sleep quality.

In one embodiment, the patient to be treated suffers from or is in the risk of suffering from hypertension.

In one embodiment, the compound of the invention is administered in an amount of from about 0.001 to about 100 mg/kg body weight per day.

A typical oral dosage is in the range of from about 0.001 to about 100 mg/kg body weight per day, preferably from about 0.01 to about 50 mg/kg body weight per day. The exact dosage will depend upon the frequency and mode of administration, the sex, age, weight and general condition of the subject treated, the nature and severity of the condition treated and any concomitant diseases to be treated and other factors evident to those skilled in the art.

A typical oral dosage for adults is in the range of 0.1-50 mg/day of a compound of the present invention, such as 0.5-30 mg/day, or 0.5-25 mg/day. This may typically be achieved by the administration of 0.1-50 mg, such as 0.5-30 mg, such as 0.5, 1, 5, 10, 20 or 30 mg of the compound of the present invention.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder comprising the administration of a compound of the present invention. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

Typically, the treatment of the present invention will involve daily administration of the compounds of the present invention. This may involve once daily administration, or administration twice a day or even more frequently.

In one embodiment, the invention relates to the use of a compound of the present invention in therapy.

In one embodiment, the invention relates to the use of a compound of the present invention in the preparation of a medicament for the treatment of a disease which will benefit from an increase in the serotonin and/or noradrenaline levels in the brain.

In one embodiment, the invention relates to the use of a compound of the present invention for the preparation of a medicament for the treatment of affective disorders, depressive disorder, anxiety disorders, major depressive disorder, postnatal depression, melancholia, dysthymia, depression associated with bipolar disorder, Alzheimer's, psychosis, Huntington's Disease, multiple sclerosis or Parkinson's, general anxiety disorder, social anxiety disorder, post traumatic stress disorder, obsessive compulsive disorder, panic disorder, panic attacks, specific phobias, social phobia, agoraphobia, ADHD, hot flushes, stress urinary incontinence, burn-out/stress, pain, chronic pain, fibromyalgia, tension-type headache, neuropathic pain, overall pain, low back pain, shoulder pain, pain while awake, pain during daily activities, osteoarthritis and cancer pain.

In one embodiment, the invention relates to compounds of the present invention for use in the treatment of affective disorders, depressive disorder, anxiety disorders, major depressive disorder, postnatal depression, melancholia, dysthymia, depression associated with bipolar disorder, Alzheimer's, psychosis, Huntington's Disease, multiple sclerosis or Parkinson's, general anxiety disorder, social anxiety disorder, post traumatic stress disorder, obsessive compulsive disorder, panic disorder, panic attacks, specific phobias, social phobia, agoraphobia, ADHD, hot flushes, stress urinary incontinence, burn-out/stress; pain, chronic pain, fibromyalgia, tension-type headache, neuropathic pain, overall pain, low back pain, shoulder pain, pain while awake, pain during daily activities, osteoarthritis and cancer pain.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, drops, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 50 mg, such as 0.5 mg, 1 mg, 5 mg or 10 mg of a compound of the present invention.

For parenteral routes such as intravenous, intrathecal, intramuscular and similar administration, typically doses are in the order of about half the dose employed for oral administration.

For parenteral administration, solutions of the compound of the invention in sterile aqueous solution, aqueous propylene glycol, aqueous vitamin E, aqueous cyclodextrin, or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are microcrystalline cellulose, starch, gums, lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene, cyclodextrin and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, drops, a solution or suspension in an aqueous or non-aqueous liquid, or an oil-in-water or water-in-oil liquid emulsion.

If a solid carrier is used for oral administration, the preparation may be a tablet in powder or pellet form or in the form of a troche or lozenge. Alternatively, tablets, powders and pellets may be placed in a hard gelatine capsule. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents and subsequently compressing the mixture in a conventional tabletting machine. Adjuvants or additives usually used for purposes such as colouring, flavouring, preservation etc. may be used.

Capsules comprising a compound of the present invention may be prepared by mixing a powder comprising said compound with e.g. microcrystalline cellulose and magnesium stearate and place said powder in a hard gelatine capsule. Optionally, said capsule may be coloured by means of a suitable pigment. Typically, capsules will comprise 0.1-10% of a compound of the present invention, such as 0.15-0.25%, 0.3-0.4%, 1.6-1.8%, and 3.3-3.5% of a compound of the present invention—calculated as the free base. These strengths can be used to conveniently deliver 0.5, 1, 5 and 10 mg of a compound of the present invention in a unit dosage form.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

The free base of the present invention may be prepared as disclosed in WO 2005/061455. Salts of the present invention may be prepared by dissolving the free base in an appropriate solvent, adding the relevant acid, followed by precipitation. Precipitation may be accomplished either by the addition of a second solvent, and/or evaporation, and/or cooling. Alternatively, the compounds may be synthesized as depicted below Step 1

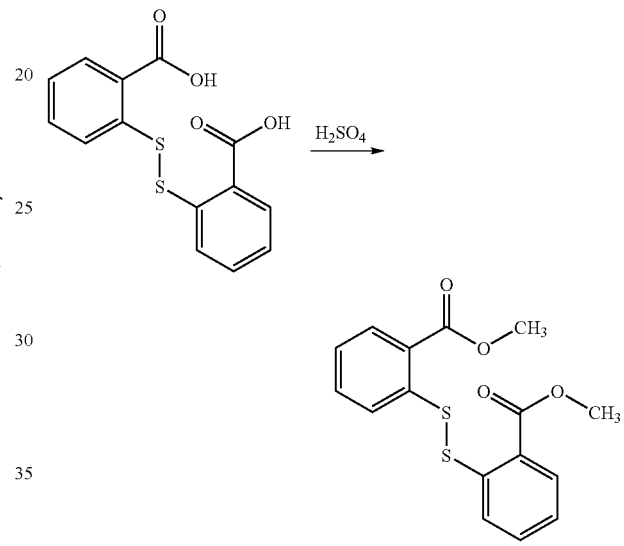

In step 1, 1 equivalent of 2,2-dithiobenzoic acid is mixed with 1.5-2.5 equivalent $H_2SO_4$, such as 2 equivalents, in methanol. The reaction is carried out at reflux temperature.

Step 2

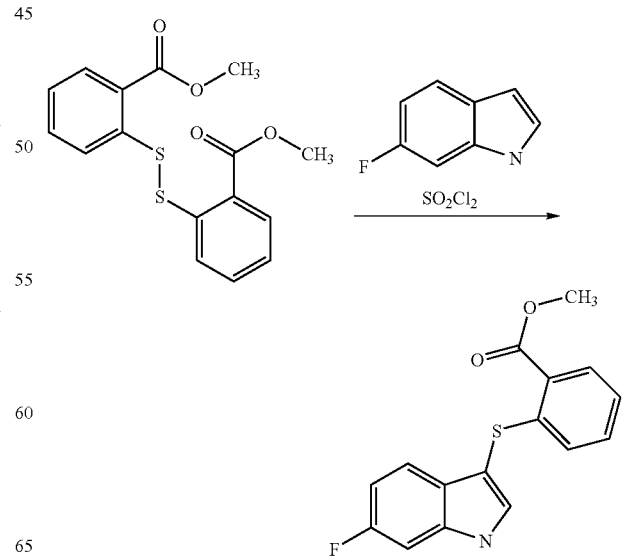

In step 2, 1 equivalent of the di-benzoic acid ester is suspended in DME under a protective atmosphere, such as $N_2$, and cooled to 10-15° C. upon which sulfurylchloride in DME in slight excess (1-1.3 equivalent) is added slowly while maintaining the temperature below 25° C. Following that, 6-fluoro-indole (around 2 equivalents) in DME cooled to 10-15° c. is added still maintaining the temperature below 25° C. To complete the reaction, the mixture is heated to around 50° C. for 1-3 hours. The product from step 2 may be recovered be diluting the reaction mixture with EtOAc followed by a washing step with $NaHCO_3$ and NaCl. The organic phase was concentrated and co-evaporated with toluene. After inoculation with crystals and cooling, the product from step 2 is obtained as a precipitate.

Step 3

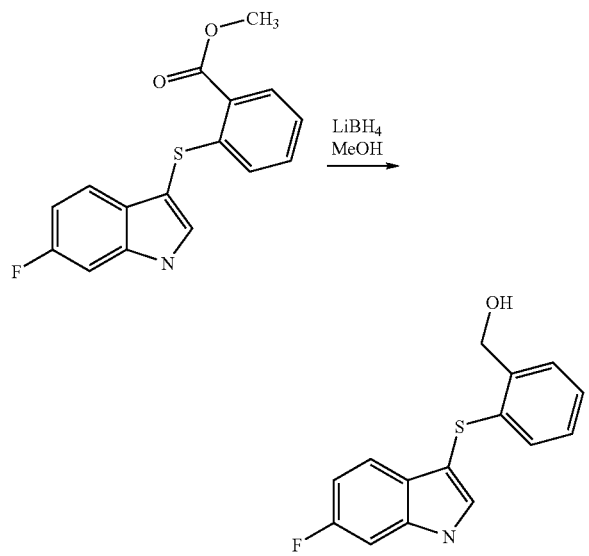

In step 3, the ester dissolved in THF (1 equivalent) is added $LiBH_4$ slowly at around 2.5 equivalents. After addition, the temperature is raised to around 40° C. Around 2.5 equivalents of methanol is then added slowly while maintaining the temperature below 55° C. After completion of the reaction (~2 hours), citric acid (around 2.5 equivalents) is added to remove excess $LiBH_4$. The organic phase is collected, concentrated and co-evaporated with iso-propanol. The mixture obtained is added slowly to water to allow precipitation, which precipitate is collected.

Step 4

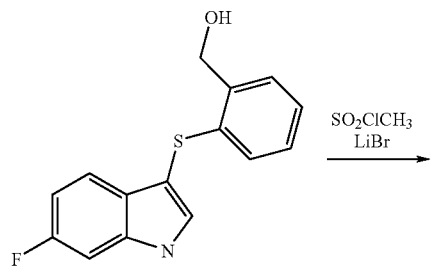

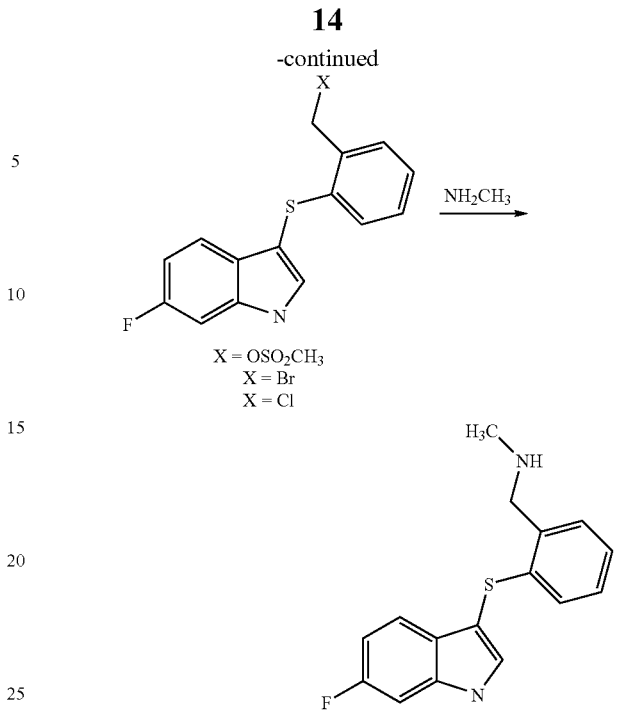

In step 4, 1 equivalent of the benzyl alcohol dissolved in THF is added around 1.2 equivalent LiBr and around 1.5 equivalent NN-diisopropyl ethylamine (DIPEA). To this mixture, around 1.4 equivalent $SO_2ClCH_3$ dissolved in THF is added while keeping the temperature below 50° C. The mixture is stirred for 15-20 hours to complete the reaction. To the mixture obtained, around 40 equivalents of $NH_2CH_3$ is added slowly, and the reaction is allowed to complete at around 40-45° C. for approximately 5 hours. At this step, an appropriate acid may be added to afford the corresponding acid addition salt. In particular, the addition of around 1.4 equivalent L-(+) tartaric acid will effect the precipitation of [2-(6-fluoro-1H-indol-3-ylsulfanyl)benzyl]methyl amine L-(+)-hydrogen tatrate salt.

In one embodiment, the invention provides compounds which are useful in the manufacture of compounds of the present invention.

In on embodiment, the invention provides the compound 2-(6-fluoro-1H-indol-3-ylsulfanyl)-benzoic acid methyl ester, i.e.

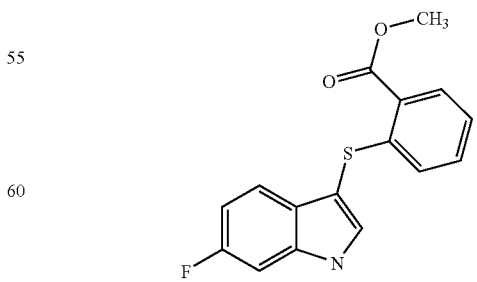

In one embodiment, the invention provides the compound [2-(6-Fluoro-1H-indol-3-ylsulfanyl)-phenyl]-methanol, i.e.

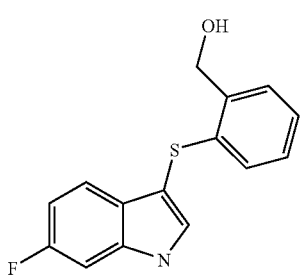

In one embodiment, the invention provides the compounds methanesulfonic acid 2-(6-fluoro-1H-indol-3-ylsulfanyl)-benzyl ester, 3-(2-chloromethyl-phenylsulfanyl)-6-fluoro-1H-indole, and 3-(2-bromomethyl-phenylsulfanyl)-6-fluoro-11H-indole, i.e.

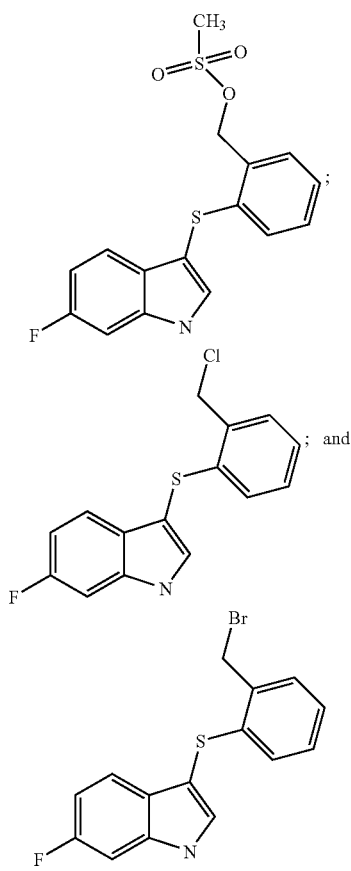

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrases "the compound" or "the compound of the invention" are to be understood as referring to various compounds of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analytical Methods $^1$H NMR spectra were recorded at 500.13 MHz on a Bruker Avance DRX500 instrument. Dimethyl sulfoxide (99.8% D) was used as solvent, and tetramethylsilane (TMS) was used as internal reference standard.

The melting points were measured using Differential Scanning Calorimetry (DSC). The equipment was a TA-Instruments DSC-Q1000 calibrated at 5°/min to give the melting point as onset value. About 2 mg of sample was heated 5°/min in a loosely closed pan under nitrogen flow.

Thermo gravimetric analysis (TGA) used for estimation of solvent/water content of dried material was performed using a TA-instruments TGA-Q500. 1-10 mg sample was heated 10°/min in an open pan under nitrogen flow.

X-Ray powder diffractograms were measured on a PANalytical X'Pert PRO X-Ray Diffractometer using CuK$_{\alpha 1}$ radiation. The samples were measured in reflection mode in the 2θ-range 5-40° using an X'celerator detector.

CHN content analysis (CHN) was measured on an Elementar Vario EL instrument from Elementar. About 4 mg of sample was used for the experiments.

Example 1

Serotonin and Noradrenalin Transport Inhibition

Aliquots of test compound and rat cortical synaptosome preparation were pre-incubated for 10 min/37° C., and then added [$^3$H]NE or [$^3$H]5-HT (final concentration 10 nM). Non-specific uptake was determined in the presence of 10 μM talsupram or citalopram and the total uptake was determined in the presence of buffer. Aliquots were incubated for 15 minutes at 37° C. After the incubation [$^3$H]NE or [$^3$H]5-HT taken up by synaptosomes was separated by filtration through Unifilter GF/C, presoaked in 0.1% PEI for 30 minutes, using a Tomtec CellHarvester program. Filters were washed and counted in a Wallac MicroBeta counter.

The compounds of the present invention revealed to be potent inhibitors of both the serotonin reuptake and the noradrenalin reuptake with IC$_{50}$ values of 0.4 nM and 4.4 nM, respectively, determined using compound concentrations covering three decades.

Example 2

5-HT$_{2A}$ Antagonism

Compounds of the present invention were tested for affinities towards serotonin receptors and was found to exhibit an antagonistic profile with high affinity at 5-HT$_{2A}$ receptors (K$_i$ 14 nM). The affinity (K$_i$ 14 nM) is calculated from $Y=100/(1+10^{(X-logIC_{50})})$ where Y denotes % binding and X denotes the concentration of compound. 5 concentration of compound (1, 10, 30, 100, 1000 nM) were used to calculate the IC50 value. K$_i$ was calculated from the Cheng Prusoff equation K$_i$=(IC$_{50}$/(1+([L]/Kd)) Affinity was determined at MDL Pharmaservices catalogue number 271650.

In a functional assay compounds of the present invention antagonises 5-HT$_{2A}$ evoked release of Ca$^{2+}$ from intracellular stores and a schild analysis revealed competitive antagonism with a pA2 value of 6.88 corresponding to Kb of 130 nM. The experiment was carried out as follows. 2 or 3 days before the experiment CHO cells expressing approximately 250 fmol/mg 5-HT$_{2A}$ receptors are plated at a density sufficient to yield a mono-confluent layer on the day of the experiment. The cells are dye loaded (Ca$^{2+}$-kit from Molecular Devices) for 60 minutes at 37° C. in a 5% CO$_2$ incubator at 95% humidity. Basal fluorescence was monitored in a fluorometric imaging plate reader or FLIPR$^{384}$ from Molecular Devices (Sunnyvale, Calif.) with an excitation wavelength of 488 nm and an emission range of 500 to 560 nm. Lacer intensity was set to a suitable level to obtain basal values of approximately 8000-10000 fluorescence units. The variation in basal fluorescence should be less than 10%. EC$_{50}$ values are assessed using increasing concentrations of test compound covering at least 3 decades. pA2 values are assessed challenging full dose response curves of 5-HT with four different concentrations of compound (150, 400 1500 and 4000 nM). Kb values were also assessed challenging 2 decades of concentrations of test substances with EC$_{85}$ of 5-HT. Test substances are added to the cells 5 minutes before the 5-HT. K$_i$ values are calculated using Cheng-Prusoff equation. In both cases a Kb of 130 nM was achieved.

Example 3

α$_{1A}$ Receptor Antagonism

Compounds of the present invention were tested for affinities towards the α$_{1A}$ receptor and was found to exhibit an antagonistic profile with high affinity, K$_i$ 14 nM.

On the day of the experiments membranes (see below for description of membrane preparation) are thawed and homogenized in buffer using an ultra turrax and diluted to the desired concentration (5 μg/well~5 μg/900 μl, store on ice until use).

The experiment is initiated by mixing of 50 μl test compound, 50 μl [$^3$H]-Prazosin and 900 μl membranes, and the mixture is incubated for 20 minutes at 25° C. Non-specific binding is determined in the presence of 10 μM WB-4101 and the total binding is determined in the presence of buffer. After the incubation, bound ligand is separated from unbound by filtration through Unifilter GF/B, presoaked in 0.1% PEI for 30 minutes, using a Tomtec Cell Harvester program (D4.2 . . . 4) 96 well. Filters are washed 3 times with 1 ml ice-cold buffer, dried at 50° C. and 35 μl scintillation liquid/well is added to the filters. Bound radioactivity is counted in a Wallac OY 1450 MicroBeta. The affinity (K$_i$ 10 nM) is calculated from $Y=100/(1+10^{(X-logIC_{50})})$ where Y denotes % binding and X denotes the concentration of compound. Concentrations of compound covering 2 decades were used to calculate the IC50 value. K$_i$ was calculated from the Cheng Prusoff equation K$_i$=(IC$_{50}$/(1+([L]/Kd))

In a functional assay compounds of the present invention antagonises adrenaline evoked release of Ca$^{2+}$ from intracellular stores and a functional assay revealed that compounds were antagonists with a Kb of 64 nM.

These experiments were carried out essentially as described below.

All cells were cultured in DMEM medium supplemented with 10% BCS, 4 mM L-glutamine (or 2 mM in the case of COS-7), and 100 units/ml penicillin plus 100 μg/ml streptomycin, at 37° C., in 5% CO2.

Twenty-four hours prior to assays, CHO cells expressing the human alpha1A-7 receptors were seeded into 384-well black wall microtiter plates coated with poly-D-lysine. Culture medium was aspirated and cells were dye-loaded with 1.5 μM Fluo-4 in assay buffer composed of Hank's Balanced Salt Solution (138 mM NaCl, 5 mM KCl, 1.3 mM CaCl$_2$, 0.5 mM MgCl$_2$, 0.4 mM MgSO$_4$, 0.3 mM KH$_2$PO$_4$, 0.3 mM Na$_2$HPO$_4$, 5.6 mM glucose) plus 20 mM HEPES pH 7.4, 0.05% BSA and 2.5 mM probenicid (50 μl/well) for 1 hour in 5% CO$_2$ at 37° C. After excess dye was discarded, cells were washed in assay buffer and layered with a final volume equal to 45 μl/well (or 30 ul/well for antagonist assay). In the case of antagonist evaluation, antagonist or vehicle was added at this point as a 15 μl aliquot in 4% DMSO-containing buffer at 4× the final concentration (final DMSO=1%), followed by a 20 min incubation. Basal fluorescence was monitored in a fluorometric imaging plate reader or FLIPR™ from Molecular Devices (Sunnyvale, Calif.) with an excitation wavelength of 488 nm and an emission range of 500 to 560 nm. Laser excitation energy was adjusted so that basal fluorescence readings were approximately 8,000 relative fluorescent units (RFU). Cells were then stimulated at room temperature with agonists diluted in assay buffer (15 μl), and RFU were measured at 1.5 second intervals over a period of 2.5 min. Maximum change in fluorescence was calculated for each well. Concentration-response curves derived from the maximum change in fluorescence were analyzed by nonlinear regression (Hill equation). For antagonistic determinations, after 20 min of compound incubation (as above), fixed concentrations of standard agonist serotonin were added.

Membrane Preparation

Cells were grown to 95% confluence, washed twice with buffer (50 mM Tris pH 7.7, 125 mM NaCl) and detached by scraping in a volume of 10 ml buffer/160 cm$^2$. The detached cells were centrifuged (7 min, 120×g) and the pellet was re-suspended in 8 ml buffer and homogenized (Ultra Torax). Protein concentration was measured with BCA™ (Pierce #23223+23224).

Example 4

Capsules Comprising Compound of the Present Invention

[2-(6-fluoro-1H-indol-3-ylsulfanyl)benzyl]methyl amine L-(+) hydrogen tatrate was mixed with microcrystalline cellulose in a first step. In a second step magnesium stearate was mixed in. Capsules with four strengths were prepared—the active ingredient is stated as the free base.

| | Active ingredient | | | |
|---|---|---|---|---|
| | 0.5 mg | 1 mg | 5 mg | 10 mg |
| Hydrogen tatrate salt | 7.62 g | 15.24 | 76.2 | 152.4 |
| Microcrystalline cellulose | 2794.1 g | 2776.56 | 2804.7 | 2748.3 |
| Magnesium stearate | 28.3 g | 28.2 | 29.1 | 29.3 |
| Weight of capsule content | 283 mg | 282 | 291 | 293 |

10.000 capsules were prepared from each batch.

Example 5

Impact on Sleep Architecture

Rats were implanted with EEG and EMG electrodes to monitor the brain electrical activity and the muscle electrical activity, respectively. The electrodes were connected to a radio transmitter allowing a continuous collection of activity data from freely moving, undisturbed and home-caged animals. The EEG and EMG data were visually scored to determine the arousal states wake, SWS and REM sleep. A group of 10 rats were administered vehicle or the compound of the present invention corresponding to 0.4 mg/kg and 4 mg/kg of the free base. A William's square cross over design was applied so that each animal receives each treatment once.

The table below shows the % of time spent in each arousal state during the second hour of recording, i.e. one to two hours post injection.

| | Wake | SWS | REM |
|---|---|---|---|
| Vehicle | 32.64 | 57.22 | 10.14 |
| 0.4 mg/kg | 37.92 | 62.08 | 0.00 |
| 4.0 mg/kg | 30.03 | 69.97 | 0.00 |

The table below shows the sleep latency in minutes, i.e. the time from injection of the compound until first consolidated sleeping episode.

| | Vehicle | 0.4 mg/kg | 4.0 mg/kg |
|---|---|---|---|
| Minutes | 40.11 | 26.43 | 20.62 |

Data in the above tables show that compounds of the present invention exert a REM sleep suppression, that there appears to be a dose dependent increase in the SWS sleep, and that the awakened state appears largely unaffected by the compounds of the present invention. Hence, the compounds of the present invention suppress the REM sleep as would be expected for compounds having NAT and SERT activity, however they do so without sleep disruptive effects that often accompany compounds with SERT and NAT activity. Moreover, there is a dose dependent decrease in the sleep latency, i.e. sleep commences faster after the administration of the compounds of the present invention.

These data strongly suggest that compounds of the present invention can be used in the treatment e.g. affective disorders without the accompanying adverse sleep effects experienced with compounds having SERT and/or NAT activity. The data shown here are all the more impressive as the compounds of the present invention have higher (~40 fold) $K_i$ value for the rat $5\text{-}HT_{2A}$ receptor than for the human $5\text{-}HT_{2A}$ receptor; hence any $5\text{-}HT_{2A}$ mediated effect would be expected to be more pronounced in humans than in rats.

Example 6

Effect on Blood Pressure

The cardiovascular effects of compounds of the present invention were investigated in telemeterised Beagle dogs in the doses 0.25, 0.50 and 1.0 mg/kg given by gavage. Amount of compound is calculated as the free base. Six dogs were used in the experiment, three males and three females.

The group mean systolic arterial blood pressure (ABP) was decreased in all drug-dosed groups—see table below.

| Treatment | Systolic arterial blood pressure (Change from baseline (mean ± SD)) (10-380 min) |
|---|---|
| Vehicle | 2.38 ± 4.49 |
| 0.25 mg/kg | −4.26 ± 5.98* |
| 0.50 mg/kg | −9.77 ± 5.39* |
| 1.00 mg/kg | −6.30 ± 6.63* |

*$p < 0.05$ (both gender) compared to the vehicle group.

The group mean systolic left ventricular pressure was similarly reduced in all drug treated groups—see table below. A gender effect was seen for this parameter.

| Treatment | Systolic left ventricular pressure (Change from baseline (mean ± SD)) Post-dose period I (10-380 min) |
|---|---|
| Vehicle | 1.65 ± 3.96 |
| 0.25 mg/kg | −3.82 ± 3.42$^{♀}$ |
| 0.50 mg/kg | −11.13 ± 4.05$^{♂,♀}$ |
| 1.00 mg/kg | −3.08 ± 5.37$^{♂,♀}$ |

$^{♂}p < 0.05$ (males) compared to the vehicle group.
$^{♀}p < 0.05$ (females) compared to the vehicle group.

These data show that compounds of the present invention are not associated with increases in the blood pressure, which are normally associated with compounds having an inhibitory effect on the noradrenalin reuptake. Hence, the compounds of the present invention are useful for the treatment of affective disorders, such as e.g. depression without or with only reduced cardiovascular side effects, such as increased blood pressure.

Example 7

Preparation of the Alpha Form of the L(+) Hydrogen Tartrate Salt

[2-(6-Fluoro-1H-indol-3-ylsulfanyl)-benzyl]-methyl-amine L-(+)-hydrogen tartrate (75 g) was suspended in a mixture of methanol (225 mL) and tetrahydrofuran (375 mL) and heated for 24 hours at 50° C. The mixture was cooled down to room temperature. The product was filtered off and washed with tetrahydrofuran (60 mL) and dried at 50° C. until constant weight. NMR complies with structure.

Example 8

Preparation of the Alpha Form of the L(+) Hydrogen Tartrate Salt

[2-(6-Fluoro-1H-indol-3-ylsulfanyl)-benzyl]-methyl-amine, L-(+)-hydrogen tartrate (4 g) was dissolved in water at reflux and treated with active carbon. The solution was filtered through celite, crystallised and the crystallised product filtered off. The damp product was suspended in ethanol (100 mL), heated to 50° C. and seeded with a few crystals of α-form. The suspension was stirred overnight at 50° C. The suspension was cooled in an ice bath for an hour. The product was filtered off and dried in an vacuum oven at 40° C. NMR complies with structure.

Elemental analysis: 54.85% C, 6.35% N, 4.92% H (Theory for 1:1 salt: 55.04% C, 6.42% N, 4.85% H).

Example 9

Characterisation of the Alpha Form of the L(+) Hydrogen Tartrate Salt

The alpha form of the L(+) hydrogen tartrate salt as prepared in example 7 or 8, is crystalline (XRPD)—see FIG. 1. The alpha form has a melting point of ~193° C. It absorbs <0.1% of water when exposed to high relative humidity and has a solubility of about 1.5 mg/ml in water, pH being 3.7 in the saturated solution.

Example 10

Preparation of the Beta Form of the L(+) Hydrogen Tartrate Salt of

[2-(6-Fluoro-1H-indol-3-ylsulfanyl)-benzyl]-methyl-amine (108.5 g) was dissolved in methanol (1.7 L) by warming on a hot water bath. L-(+)-tartaric acid (56.9 g) was added, and the mixture stirred overnight at ambient temperature. The suspension was cooled on an ice bath for two hours. The solid was collected by filtration and washed with cold methanol. The product was dried in vacuum at 60° C. NMR complies with structure. Elemental analysis: 54.99% C, 6.25% N, 4.91% H (Theory for 1:1 salt: 55.04% C, 6.42% N, 4.85% H).

Example 11

Characterisation of the Beta Form of the L(+) Hydrogen Tartrate Salt

The beta form of the L(+) hydrogen tartrate salt, as prepared in example 10, is crystalline (XRPD)—see FIG. 2. The beta form has a melting point of ~189° C. It absorbs about 0.6% of water when exposed to high relative humidity and has a solubility of about 2.0 mg/ml in water, pH being 3.7 in the saturated solution.

Example 12

Antimanic Effects—Sensitized Amphetamine Response in Mice

In all experiments, animals were maintained on a 12:12 light-dark cycle with lights on at 06:00 h. Food and water was available ad libitum. Animals were taken to the experimental laboratory in the afternoon the day before the experiment was conducted. All drug doses are listed as mg salt pr. kg. Blood-samples were collected within 30 minutes after the testing was finalised.

Repeated intermittent administration of amphetamine causes development of a sensitised response to a subsequent amphetamine challenge. This phenomenon has been proposed to model the chronic and progressive nature of bipolar disorder.

Animals: Male NMRI mice weighing 19-21 g were supplied from Harlan, the Netherland's. The animals were housed 4 pr. cage in makrolon cages (20×35 cm) with two plastic houses and nesting material for enrichment. The animals had 5 days adaptation to the animal-facility prior to the initiation the experiment.

Equipment: Makrolon cages (20×35 cm) placed in quadrates equipped with 5×8 infrared light sources and photocells spaced by 4 cm were used to record the locomotor activity of the animals. The light beams cross the cage 1.8 cm above the bottom of the cage. Recording of a motility count required interruption of adjacent light beams, thus avoiding counts induced by stationary movements of the mice.

Experimental set-up: The animals were pre-treated with either amphetamine sulphate 2.50 mg/kg (10 ml/kg s.c.) or vehicle for 5 consecutive days. After 11+/−1 days withdrawal period the animals were injected with test-drug or vehicle injection. Lithium chloride was dissolved in distilled water and injected s.c. (6 ml/kg) in dose of 40 mg/kg (0.94 mEq/kg), 30 minutes before testing. Test compound ([2-(6-fluoro-1H-indol-3-ylsulfanyl)benzyl]methyl amine L-(+)-hydrogen tatrate) was dissolved in 10% hydroxypropyl-beta-cyclodextrin and injected s.c. in doses of 0.08 and 0.4 mg/kg 60 minutes before testing. Owing to Test compound's lower affinity to rodent $5HT_{2A}$ receptor with respect to the human receptor, the tested doses of Test compound was combined with a dose of MDL 100907 ([R-(+)-a-(2,3-dimethoxyphenyl)-1-[2-(4-fluorophenylethyl)]-4-piperidinem ethanol]) that achieves full occupancy of this receptor. 30 minutes before testing the animals were placed in the activity boxes for habituation. After the habituation period the mice were injected with a low dose amphetamine challenge (1.25 mg/kg or saline, 10 ml/kg) and the locomotor activity were measured for 60 minutes. The mice were dosed after the average weight of 16 animals.

Pre-treatment with amphetamine (2.50 mg/kg, s.c. 5 days) resulted in a sensitised response (increased locomotor activity) to an acute low dose amphetamine challenge (1.25 mg/kg, s.c)(***P<0.001). Lithium (0.94 mEq/kg) and MDL 100907 (0.3 mg/kg) significantly decreased the induced locomotor activity (*P>0.05). Test compound 0.08 mg/kg and 0.4 mg/kg alone had no effect on the induced locomotor activity. The tested doses of Test compound, MDL 100907 and Lithium had no significant effect on baseline activity. However, combination of Test compound (0.08 mg/kg and 0.4 mg/kg) with MDL 100907 (0.3 mg/kg) resulted in significantly lowered baseline activity in saline pre-treated animals (*P<0.001)—see FIG. 3**

Example 13

Antimanic Effect—Amphetamine and Chlordiazapoxide Induced Locomotor Activity in Rats Increased locomotor activity induced by an appropriate combination of amphetamine and chlordiazepoxide is a proposed animal model of mania. The induced locomotor activity can be reversed by Lithium.

In all experiments, animals were maintained on a 12:12 light-dark cycle with lights on at 06:00 h. Food and water was available ad libitum. Animals were taken to the experimental laboratory in the afternoon the day before the experiment was conducted. All drug doses are listed as mg salt pr. kg. Blood-samples were collected within 30 minutes after the testing was finalised.

Animals: Male Wistar rats weighing 160-175 g were supplied from Harlan, the Netherlands. The animals were housed 4 pr. cage in makrolon cages (20×35 cm) with one plastic house for enrichment. The rats had 5 days adaptation to the animal facility prior to the initiation of the experiment.

Equipment: Makrolon cages (20×35 cm) placed in a U-frame equipped longitudinally with 4 infrared light sources and photocells were used to record the locomotor activity of the animals. The light beams cross the cage 4 cm above the bottom of the cage. Recording of a motility count required interruption of adjacent light beams, thus avoiding counts induced by stationary movements of the rat. A thin layer of standard bedding material coved the bottom of the cage.

Experimental set-up: Lithium Chloride was dissolved in distilled waster and injected s.c. (6 ml/kg) in dose of 0.94 mEg/kg (40 mg/kg), 210 minutes before testing. Test compound (see Example 12) was dissolved in 10% hydroxypropyl-beta-cyclodextrin and injected s.c. in dose of 0.4 mg/kg alone or combined with 0.3 mg/kg MDL 100907 60 minutes before testing. Amphetamine sulphate (1.2 mg/kg) was dissolved in 0.9% NaCl and injected s.c. (1 ml/kg) 35 minutes before the test. Chlordiazepoxide (10.0 mg/kg) was dissolved in 10% hydroxypropyl-beta-cyclodextrin and injected s.c. (5 ml/kg) immediately after the amphetamine injection. 35 minutes after the amphetamine and chlordiazepoxide injections the animals was placed individually in test-boxes and the activity was measured for 120 minutes.

Treatment with amphetamine (1.2 mg/kg) and chlordiazepoxide (10.0 mg/kg) resulted in an increased locomotor activity significantly larger then animals treated with vehicle (*$P<0.001$). Lithium (0.94 mEq/kg) and MDL 100907 (0.3 mg/kg) significantly reversed the induced locomotor activity (*$P<0.001$). Test compound 0.4 mg/kg showed a tendency to increase the locomotor activity induced activity, but not significantly. However, combination of Test compound (0.4 mg/kg) with MDL 100907 (0.3 mg/kg) resulted in a significant attenuation of the induced locomotor activity. The tested doses of Lithium, MDL 100907 and Test compound had no effect on baseline activity—see FIG. 4.

Example 14

Anxiolytic Effects

In all experiments, animals were maintained on a 12:12 light-dark cycle with lights on at 0600 h. Food and water were available ad libitum
Mouse Marble Burying For rodents, burying functions as a defensive behavior, used to lessen the intensity of a threat or the animal's vulnerability to it. Researchers have investigated defensive burying behaviour using a variety of threatening objects such as electrified prods and unpleasant tasting foods and liquids. Benign objects such as marbles and food pellets also elicit burying behaviour. Mice probably bury harmless objects because they are novel, and are therefore perceived as threatening. Acute administration of both anxiolytic and antidepressant drugs reduce the number of marbles buried in this paradigm.

Male BALB/cByJ mice (22-28 g) were housed 5/cage. Two experiments were performed. Mice received vehicle or 0.625, 1.25, or 5 mg/kg (s.c.) Test compound (see example 12). 30 minutes after injection, animals were placed individually in cages containing 20 marbles (2 rows of 10) on top of 1.5 inches of Aspen bedding. After a 30-minute test period, mice were returned to their home cages, and the number of visible marbles (less than ⅔ covered with bedding) were counted and subtracted from 20 to give number of marbles buried.

Figure 5:
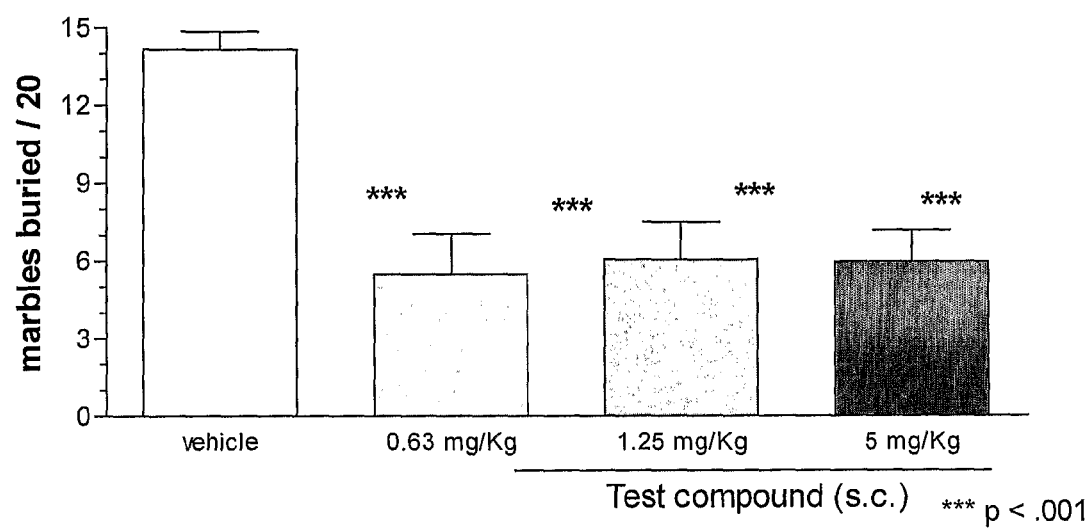

The numbers of marbles buried was significantly and equivalently reduced by pretreatment with all three doses of Test compound (N=9-11/group)—see FIG. 5.
Stress-Induced Hyperthermia The stress-induced hyperthermia (SIH) test is based upon the principle that, like other mammals, mice have a natural hyperthermic response to stress. In this paradigm, the stressor is having the rectal temperature taken. This physiological response is considered to reflect the anxiety level of the animal, and is attenuated by pretreatment with anxiolytic drugs such as benzodiazepines.

Male C57B1/6 mice (18-21 g) were housed 5/cage until 1 day before the experiment, at which time they were brought to the testing room and singly-housed. Testing was conducted over a two-day period from 9-12 am. Mice received vehicle, chlordiazepoxide (10 mg/kg), or 0.02, 0.08, or 0.32 mg/kg Test compound (s.c.). One hour later, core temperature was measured with a rectal probe (T1) and each animal was returned to its cage. Ten minutes later, a second reading was obtained (T2). The difference between the two readings (T2−T1) was calculated as the measure of stress-induced hyperthermia.

Figure 6:
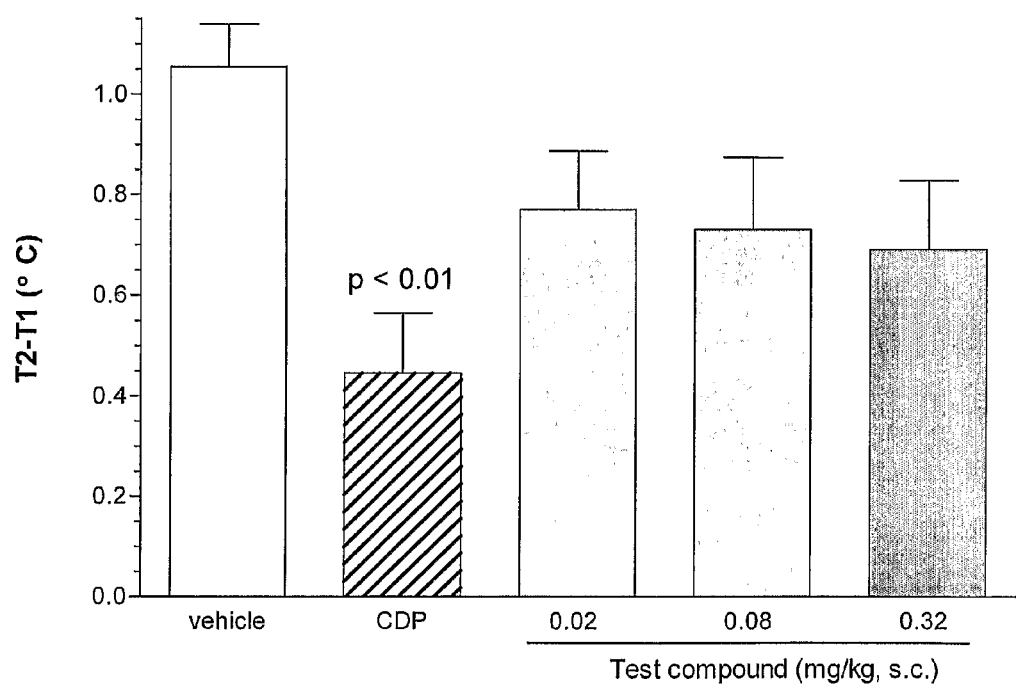

The increase in core temperature between the first and second measurements, i.e. stress-induced hyperthermia (SIH), was significantly reduced by pretreatment with CDP ($p<0.01$), and in an dose-dependent manner following treatment with Test compound—see FIG. 6.

Example 13

Crystalline Salts of
[2-(6-fluoro-1H-indol-3-ylsulfanyl)benzyl]methyl amine

Dissolving 5 grams of [2-(6-fluoro-1H-indol-3-ylsulfanyl) benzyl]methyl amine in 100 ml EtOH produced a 0.175 M stock-solution in EtOH from which aliquots of 2.0 ml (100 mg of base) was used.

Dissolving 5 grams of [2-(6-fluoro-1H-indol-3-ylsulfanyl) benzyl]methyl amine in 125 ml THF produced a 0.140 M stock-solution in THF from which aliquots of 2.5 ml (100 mg of base) was used.

The given aliquots were placed in test tubes and while stirred, 1.00 equivalent amount of acid was added. If the acid was a liquid it was added neat otherwise it was dissolved in the given solvent prior to addition. After mixing and precipitation stirring was continued overnight and the precipitate collected by filtration. The precipitate was dried overnight at room temperature without vacuum.

The table below summarizes characteristics of the individual salts.

| Acid (Base:Acid) | MW (g/mol) | %C %H %N (Found) | %C %H %N (Theory) | TGA % weight loss (-> Temp) | DSC ($T_{ons}$/$T_{peak}$) °C. | Solvent | XRPD crystal form and comments |
|---|---|---|---|---|---|---|---|
| L(+) tartrate 1:1 | 150.1 | 55.09 6.41 4.89 | 55.04 6.42 4.85 | <0.1 (150 C.) | 194.3/194.4 | EtOH | α |
| L(+) tartrate 1:1 | 150.1 | 54.99 6.25 4.91 | 55.04 6.42 4.85 | <0.1 (150 C.) | 189.8/190.1 | MeOH | β |
| Acetic Acid 1:1 salt | 60.1 | 62.40 8.06 5.63 | 62.40 8.09 5.53 | 17 (160 C.) | 178.3/178.9 | EtOH | α |
| Acetic Acid 1:1 salt | 60.1 | 62.08 7.74 5.75 | 62.40 8.09 5.53 | 18.8 (156 C.) | No melting peak | THF | β |
| Propionic acid 1:1 salt | 74.1 | 63.24 7.74 5.94 | 63.31 7.77 5.87 | 20 (145 C.) | 177.9/179.4 | EtOH | α |
| 2,2 dimethyl propionic acid 1:1 salt | 102.1 | 64.96 6.38 7.00 | 64.92 7.21 6.49 | 21.0 (117 C.) | 101.5/115.4 | THF | Crystalline, mixture/solvate |
| 2-Hydroxyisobutyric acid 1:1 | 104.1 | 61.48 7.12 6.01 | 61.52 7.18 5.94 | <0.1 (121 C.) | 173.2/173.9 | EtOH | α |
| Adipic acid, 1,6-hexanedioic acid 2:1 | 146.14 | 63.06 7.54 5.83 | 63.48 7.80 5.61 | 2.6 (175 C.) | 210.4/210.5 | EtOH | α + β |
| Adipic acid, 1,6-hexanedioic acid 2:1 | 146.14 | 63.26 7.67 5.73 | 63.48 7.80 5.61 | 0.2 (165 C.) | 208.2/208.8 | EtOH | β |
| Fumaric acid 2:1 | 116.07 | 62.58 8.11 5.02 | 62.77 8.14 4.98 | <0.1 (152 C.) | 192.5/194.2 | EtOH | α + β |
| Fumaric acid 2:1 | 116.07 | 62.70 8.07 5.05 | 62.77 8.14 5.61 | <0.1 (149 C.) | 180.8/181.6 | EtOH | α |
| Fumaric acid (mixture) | 116.07 | 62.73 7.05 5.76 | 59.69 6.96 4.76 | 10.5 (153 C.) | 189.2/191.3 | THF | Crystalline; mixture/solvate |
| Glutaric acid, 1,5-pentanedioic acid 2:1 | 132.12 | 62.91 7.80 5.56 | 63.05 7.95 5.43 | <0.1 (134 C.) | 160.7/161.1 | EtOH | α |
| Maleic acid 2:1 | 116.1 | 62.56 8.05 5.09 | 62.77 8.13 5.98 | <0.1 (137 C.) | 163.2/165.0 | EtOH | α |
| Maleic acid (mixture) | 116.1 | 59.03 5.95 5.44 | | 9.8 (100 C.) | 163.0/164.3 | THF | Crystalline; mixture/solvate |
| Malonic acid 2:1 | 104.0 | 61.78 8.19 5.14 | 62.11 8.28 5.06 | 18.9 (214 C.) | 207.8/207.9 | EtOH | α |
| Oxalic acid 2:1 | 90.0 | 60.81 8.23 4.95 | 61.62 8.45 4.87 | 0.2 (158 C.) | 207.9/207.9 | EtOH | α |
| Oxalic acid (mixture) | 90.0 | 58.82 6.82 5.35 | | 8.0 (150 C.) | 185.8/186.3 | THF | Partly Crystalline; mixture/solvate |
| 2-Oxoglutaric acid 2:1 | 146.09 | 61.37 7.59 5.17 | 61.82 7.79 5.05 | 10.0 (164 C.) | 148.0/153.6 | EtOH | α |
| Sebacic acid, 1,8-octanedioic acid 2:1 | 202.2 | 65.02 7.20 6.21 | 65.11 7.23 4.98 | <0.1 (147 C.) | 153.8/154.6 | EtOH | α |
| Sebacic acid, 1,8-octanedioic acid 2:1 | 202.2 | 65.02 7.14 6.31 | 65.11 7.23 4.98 | <0.1 (137 C.) | 152.9/154.4 | EtOH | β |
| Sebacic acid, 1,8-octanedioic acid (mixture) | 202.2 | 62.73 5.13 6.91 | | 3.1 (108 C.) | 85.5/91.6 | THF | Partly Crystalline; mixture/solvate |
| Succinic acid, 1,4-butanedioic acid, 2:1 | 118.1 | 62.48 8.09 5.29 | 62.58 8.11 5.25 | <0.1 (137 C.) | 180.8/181.3 | EtOH | α |
| Succinic acid, 1,4-butanedioic acid, 2:1 | 118.1 | 62.49 8.05 5.36 | 62.58 8.11 5.25 | <0.1 (152 C.) | 195.7/196.6 | EtOH | β |
| Succinic acid, 1,4-butanedioic acid, (mixture) | 118.1 | 60.78 6.93 5.59 | | 3.8 (115 C.) | 168.1/170.6 | THF | Crystalline; mixture/solvate |
| L-malic acid, L-2-hydroxy butanedioic acid 2:1 | 134.1 | 60.14 7.58 5.24 | 61.17 7.93 5.13 | <0.1 (145 C.) | 155.8/158.9 | EtOH | α and β |
| L-malic acid, L-2-hydroxy butanedioic acid 2:1 | 134.1 | 61.02 7.87 5.23 | 61.17 7.93 5.13 | <0.1 (150 C.) | 167.8/168.4 | EtOH | α |
| L-malic acid, L-2-hydroxy butanedioic acid (mixture) | 134.1 | 59.16 6.53 5.52 | | 2.2 (135 C.) | 151.2/154.7 | THF | Crystalline; mixture/solvate |
| M-tartaric acid, meso-2,3-dihydroxy butanedioic acid hydrate 2:1 | 150.1 | 59.63 7.67 5.13 | 59.82 7.75 5.02 | <0.1 (175 C.) | 209.2/209.8 | EtOH | α |
| M-tartaric acid, meso-2,3-dihydroxy butanedioic acid hydrate (mixture) | 150.1 | 60.04 6.73 5.76 | | 9.6 (164 C.) | 202.2/205.5 | THF | Crystalline; mixture/solvate |
| Glutaminic acid hydrate 1:1 | 165.15 | 42.26 9.43 6.13 | 55.86 9.31 5.80 | <0.1 (142 C.) | 185.9/189.6 | THF | Crystalline; mixture/solvate |
| Hydrogen chloride 1:1 | 36.45 | 59.37 8.36 5.25 | 59.52 8.68 5.00 | <0.1 (155 C.) | 221.9/222.5 | THF | α |
| Hydrobromic acid 1:1 | 80.90 | 52.43 7.52 4.56 | 52.32 7.63 4.39 | <0.1 (161 C.) | 205.0/205.2 | THF | α |
| Phosphoric acid (mixture) | 98.0 | 53.88 7.80 5.09 | 49.99 7.29 4.72 | 1.0 (134 C.) | 209.4/210.3 | EtOH | Partly crystalline |

X-ray powder diffractograms (XRPD) for the various salts are depicted in FIGS. 7-45. The table below summarises the major peaks in the individual diffractograms.

XRPD were measured on a PANalytical X'Pert PRO X-Ray Diffractometer using CuK$_{\alpha 1}$ radiation. The samples were measured in reflection mode in the 2θ-range 5-40° using an X'celerator detector.

Selected X-Ray Peak Positions (°2θ), 2:1 Means 2 Bases to 1 Acid. All Values +−0.1°

| Salt | 1 | 2 | 3 | 4 |
|---|---|---|---|---|
| L(+) hydrogen tartrate α | 9.66 | 14.53 | 18.14 | 30.48 |
| L(+) hydrogen tartrate β | 5.91 | 10.05 | 20.43 | 36.04 |
| Acetate 1:1 α | 8.96 | 13.73 | 21.10 | 27.08 |
| Acetate 1:1 β | 6.81 | 11.19 | 20.46 | 21.82 |
| Propionate 1:1 α | 9.38 | 10.83 | 27.78 | 34.79 |
| Hydroxyisobutyric acid 1:1 α | 5.91 | 20.19 | 26.57 | 37.07 |
| Adipinic acid salt 2:1 α | 8.83 | 11.04 | 30.16 | 31.66 |
| Adipinic acid salt 2:1 β | 13.51 | 20.60 | 24.66 | 29.18 |
| Adipinic acid salt 2:1 γ | 9.62 | 11.53 | 19.84 | 29.71 |
| Fumarate 2:1 α | 8.15 | 18.95 | 20.06 | 36.35 |
| Fumarate 2:1 β | 11.80 | 18.39 | 21.18 | 25.83 |
| Fumarate 2:1 γ | 14.95 | 20.63 | 20.86 | 31.15 |
| Fumarate mixture/solvate | 7.29 | 14.90 | 17.69 | 29.78 |
| Maleate 2:1 α | 9.02 | 18.05 | 19.83 | 22.53 |
| Maleate mixture/solvate | 7.28 | 10.30 | 20.68 | 29.35 |

-continued

| Salt | 1 | 2 | 3 | 4 |
|---|---|---|---|---|
| Malonate 2:1 α | 6.18 | 9.35 | 16.17 | 28.27 |
| Malate 2:1 α | 5.98 | 8.05 | 18.82 | 28.37 |
| Malate 2:1 β | 10.64 | 15.40 | 20.71 | 25.10 |
| Malate 2:1 γ | 5.69 | 17.12 | 17.98 | 28.71 |
| Malate mixture/solvate | 7.70 | 9.87 | 19.78 | 24.81 |
| Glutarate 2:1 α | 6.39 | 13.93 | 19.86 | 32.27 |
| Oxalate 2:1 α | 13.43 | 16.51 | 25.40 | 29.28 |
| Oxalate 2:1 β | 6.39 | 17.61 | 19.21 | 32.28 |
| Oxalate mixture/solvate | 6.98 | 7.72 | 18.00 | 27.44 |
| Sebacic acid salt 2:1 α | 9.60 | 14.80 | 19.82 | 22.90 |
| Sebacic acid salt 2:1 β | 9.37 | 14.94 | 18.84 | 31.13 |
| Sebacic acid salt 2:1 γ | 8.99 | 13.51 | 18.65 | 27.18 |
| Sebacic acid salt mixture/solvate | 7.24 | 8.02 | 14.50 | 21.76 |
| Succinate 2:1 α | 9.37 | 15.77 | 20.85 | 31.13 |
| Succinate 2:1 β | 9.60 | 16.29 | 19.82 | 32.03 |
| Succinate 2:1 γ | 8.17 | 19.00 | 24.05 | 26.98 |
| Succinate mixture/solvate | 7.28 | 11.23 | 16.92 | 26.61 |
| Hydrochloride 1:1 α | 14.04 | 16.94 | 24.37 | 29.64 |
| Hydrobromide 1:1 α | 5.92 | 8.28 | 20.93 | 29.91 |
| M-tartrate 2:1 α | 6.21 | 18.66 | 20.33 | 24.20 |
| M-tartrate mixture/solvate | 10.03 | 16.22 | 23.26 | 27.10 |
| 2-Oxogluterate 2:1 α | 6.37 | 13.93 | 17.30 | 30.42 |
| Phosphate mixture/solvate | 5.88 | 7.62 | 17.99 | 25.67 |
| 2,2 Dimethyl propionic acid salt, mixture/solvate | 6.25 | 16.11 | 21.29 | 29.34 |
| Glutaminic acid salt mixture/solvate | 13.61 | 21.29 | 25.78 | 32.79 |

The invention claimed is:

1. A crystalline form of the compound [2-(6-fluoro-1H-indol-3-ylsulfanyl)benzyl]methyl amine L-(+)-hydrogen tartrate salt.

2. The crystalline form according to claim 1 with an X-ray diffraction pattern as shown in FIG. 1.

3. The crystalline form according to claim 1 with an X-ray diffraction pattern as shown in FIG. 2.

4. A pharmaceutical composition comprising the crystalline form according to claim 1 and a pharmaceutical acceptable carrier or excipient.

5. A compound selected from
2-(6-Fluoro-1H-indol-3-ylsulfanyl)-benzoic acid methyl ester;
[2-(6-Fluoro-1H-indol-3-ylsulfanyl)-phenyl]-methanol;
Methanesulfonic acid 2-(6-fluoro-1H-indol-3-ylsulfanyl)-benzyl ester;
3-(2-chloromethyl-phenylsulfanyl)-6-fluoro-1H-indole; and
3-(2-bromomethyl-phenylsulfanyl)-6-fluoro-1H-indole.

6. The crystalline form according to claim 1 with an X-ray powder diffraction pattern characterized by major peaks (degrees 2θ) at 9.66, 14.53, 18.14 and 30.48.

* * * * *